(12) United States Patent
Ishigami et al.

(10) Patent No.: US 8,308,637 B2
(45) Date of Patent: Nov. 13, 2012

(54) ENDOSCOPE

(75) Inventors: Takakazu Ishigami, Tama (JP); Yoichi Hosaka, Iruma (JP)

(73) Assignee: Olympus Corporation, Tokyo (JP)

( * ) Notice: Subject to any disclaimer, the term of this patent is extended or adjusted under 35 U.S.C. 154(b) by 1709 days.

(21) Appl. No.: 11/398,543

(22) Filed: Apr. 6, 2006

(65) Prior Publication Data

US 2006/0183977 A1    Aug. 17, 2006

Related U.S. Application Data

(63) Continuation of application No. PCT/JP2004/014617, filed on Oct. 4, 2004.

(30) Foreign Application Priority Data

Oct. 6, 2003   (JP) ................ 2003-347645

(51) Int. Cl.
*A61B 1/06* (2006.01)
*A61B 1/00* (2006.01)
*A61B 1/04* (2006.01)

(52) U.S. Cl. ................ 600/177; 600/129

(58) Field of Classification Search ............. 600/172, 600/175, 177, 178, 180, 129
See application file for complete search history.

(56) References Cited

U.S. PATENT DOCUMENTS

| | | | | |
|---|---|---|---|---|
| 4,301,790 A * | 11/1981 | Bol et al. | | 600/109 |
| 4,860,732 A * | 8/1989 | Hasegawa et al. | | 600/109 |
| 5,531,664 A * | 7/1996 | Adachi et al. | | 600/149 |
| 6,095,970 A * | 8/2000 | Hidaka et al. | | 600/110 |
| 6,449,006 B1 * | 9/2002 | Shipp | | 348/70 |
| 6,796,939 B1 * | 9/2004 | Hirata et al. | | 600/179 |
| 2003/0035048 A1 * | 2/2003 | Shipp | | 348/68 |
| 2004/0199052 A1 * | 10/2004 | Banik et al. | | 600/142 |

FOREIGN PATENT DOCUMENTS

| | | |
|---|---|---|
| JP | 53-43989 | 4/1978 |
| JP | 59-175194 | 10/1984 |
| JP | 60-72528 | 4/1985 |
| JP | 02-160211 | 6/1990 |
| JP | 08-104026 | 4/1996 |
| JP | 10-229966 | 9/1998 |
| JP | 11-216113 | 8/1999 |
| JP | 11-267099 | 10/1999 |
| JP | 2000-089130 A | 3/2000 |
| JP | 2001-037712 | 2/2001 |
| JP | 2001-061777 | 3/2001 |
| JP | 2002-000562 | 1/2002 |
| JP | 2002-051971 | 2/2002 |
| JP | 2002-177197 | 6/2002 |
| JP | 2002-224015 | 8/2002 |
| JP | 2003-024276 | 1/2003 |

* cited by examiner

*Primary Examiner* — Philip R Smith
(74) *Attorney, Agent, or Firm* — Dickstein Shapiro LLP

(57) ABSTRACT

An endoscope includes light emitting devices arranged in the distal end portion of its insertion unit, and at least one elongated heat-radiating member. One end of the radiating member is arranged in the vicinity of the light emitting devices and the other end is arranged in a predetermined position adjacent to the proximal end of the insertion unit. In observation using the endoscope, a decrease in the amount of illumination rays or the occurrence of image noise can be prevented, the decrease and the noise being caused due to heat generated by LED illumination lights arranged at the distal end of the insertion unit. Therefore, observation can be performed for a long time in good conditions.

13 Claims, 32 Drawing Sheets

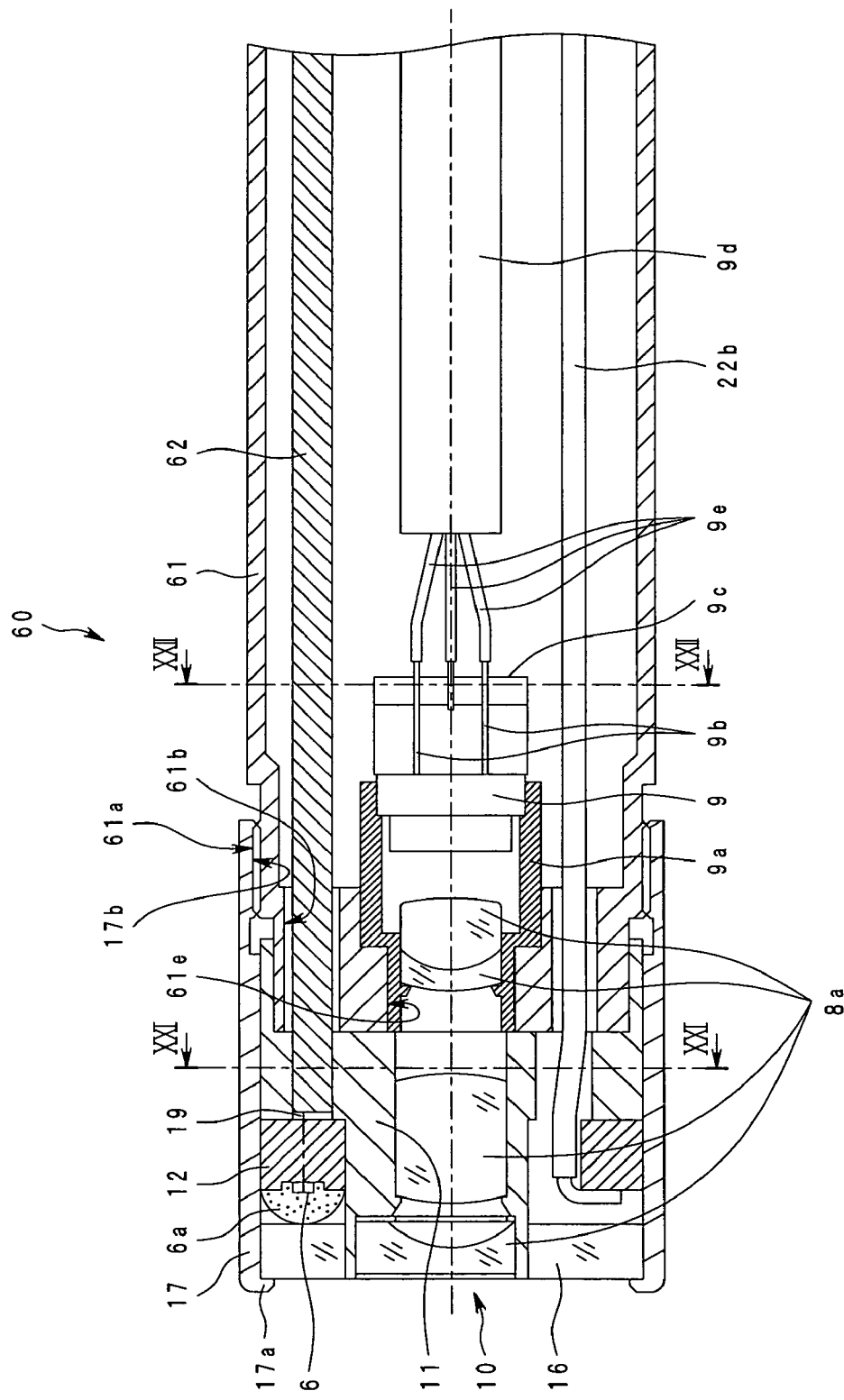

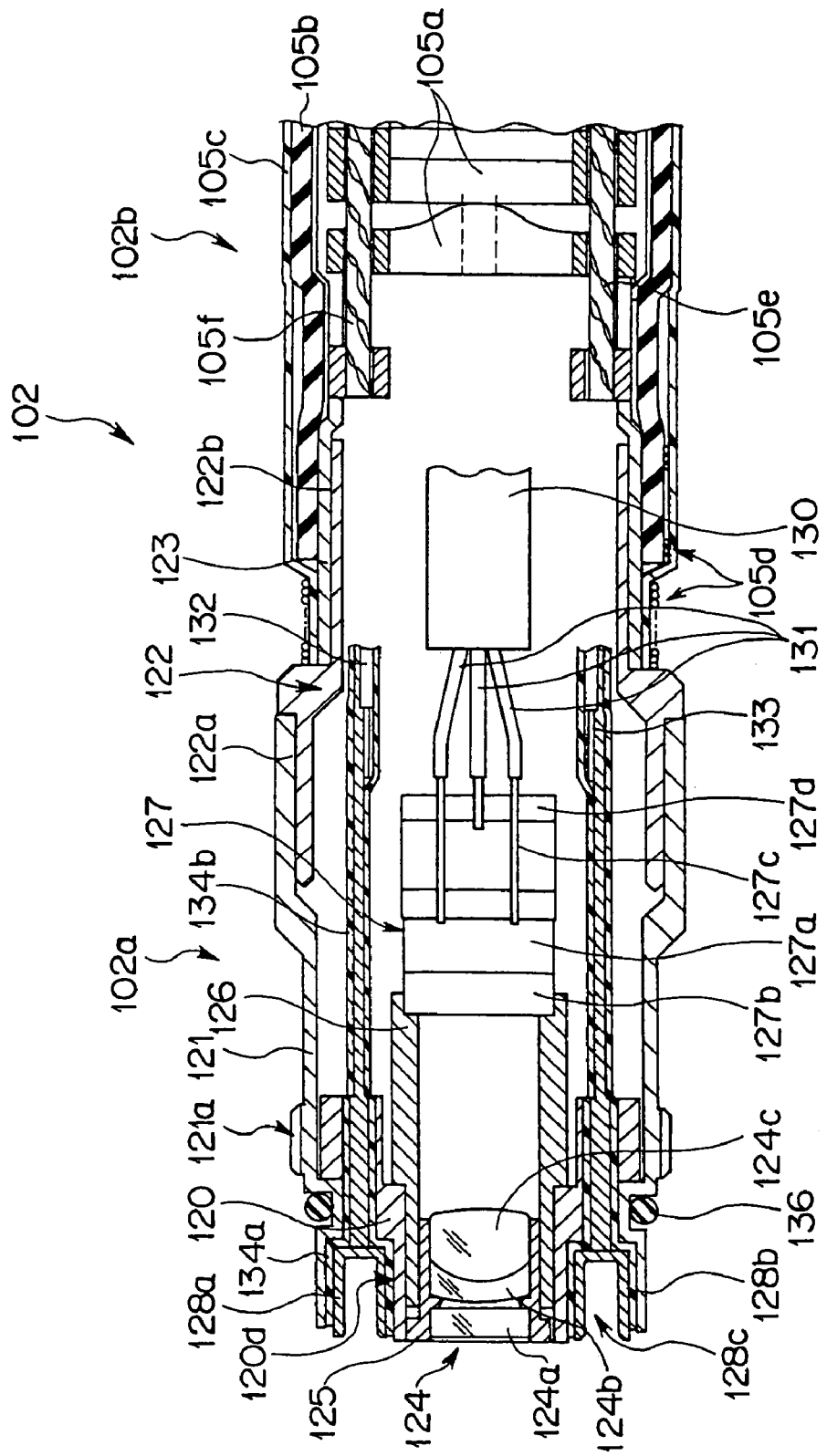

119a 113 119 114 155 154 128 134a 134b 119a 113 119 114 156 128 134a 134b 119 114a 114c 128c 134a 128 134b 114b 111 120

ENDOSCOPE

CROSS REFERENCES TO RELATED APPLICATIONS

This application is a continuation application of PCT/JP2004/014617 filed on Oct. 4, 2004 and claims benefit of Japanese Application No. 2003-347645 filed in Japan on Oct. 6, 2003, the entire contents of which are incorporated herein by this reference.

BACKGROUND OF THE INVENTION

1. Field of the Invention

The present invention relates to an endoscope using light emitting devices, serving as an illumination optical system, and an endoscope to which an adapter using light emitting devices serving as an illumination optical system is attachable.

2. Description of the Related Art

Endoscopes are widely used in the medical and industrial fields. Objects to be inspected using endoscopes are in living bodies and plants. Therefore, each endoscope requires a light source for illuminating an observation object.

General endoscope apparatuses each provide a light source, serving as an external device for an endoscope. Illumination rays emitted from the light source are supplied to a light guide disposed in the endoscope. The supplied illumination rays are transmitted through the light guide and are then emitted from an illumination window arranged at the distal end of an insertion unit, thus illuminating an observation area.

A recently proposed endoscope has an LED illumination system at the distal end of its insertion unit instead of the combination of a light source for illuminating an observation area and a light guide fiber. According to this endoscope, an observation area is directly illuminated by light emitted from the LED illumination system. In addition, the endoscope captures, using a solid-state image pickup device, an image of an observation area illuminated by light emitted from the LED illumination system. The above-described technique realizes a high functional endoscope having a small-diameter insertion unit and a simple structure.

Japanese Unexamined Patent Application Publication No. 2002-51971 discloses an endoscope in which the amount of illumination rays of an LED illumination system is increased, the system being arranged at the distal end of an insertion unit.

According to a known technique, to observe an observation area illuminated by illumination rays or the like using an endoscope, an adapter for changing optical characteristics, such as the direction of view and the angle of view, depending on the purpose of observation, is attached to the distal end of an insertion unit of the endoscope. In other words, a distal-end adapter is attached to the distal end of the insertion unit, thus achieving various observations using one endoscope. Therefore, when the above-described LED illumination system is arranged to the adapter, the usability of the endoscope can be improved.

SUMMARY OF THE INVENTION

According to the present invention, there is provided an endoscope including: light emitting devices arranged in its distal end portion; and at least one elongated heat-radiating member, one end of the member being arranged in the vicinity of the light emitting devices, the other end being arranged in a predetermined position adjacent to the proximal end of the insertion unit.

According to the present invention, there is provided an endoscope specifically including: a distal-end adapter including light emitting devices constituting an illumination optical system, a substrate for the light emitting devices, a support member for supporting the substrate, a first heat-conducting member through which heat generated by the light emitting devices is conducted, and an objective optical system constituting an observation optical system, the light emitting devices being arranged in one surface of the distal-end adapter, the substrate having a first electric connecting unit for the light emitting devices which is arranged in the other surface of the distal-end adapter; and an insertion unit having a distal end portion from which the distal-end adapter is detachable, the distal end portion including an image pickup device constituting the observation optical system, a second electric connecting unit which is electrically connected to the first electric connecting unit in the substrate, a second heat-conducting member through which the heat transferred through the first heat-conducting member is further conducted, and a heat-radiating member for radiating the heat conducted through the second heat-conducting member from the distal end portion in the direction toward the proximal end of the endoscope.

BRIEF DESCRIPTION OF THE DRAWINGS

FIG. 20 is a sectional view at the line XX-XX of FIG. 19;

FIG. 32 is sectional view at the line XXXII-XXXII of FIG. 31;

DESCRIPTION OF THE PREFERRED EMBODIMENTS

Embodiments of the present invention will be described below with reference to the drawings.

A first embodiment of the present invention will now be described with reference to FIGS. 1 to 14.

Figure 2:
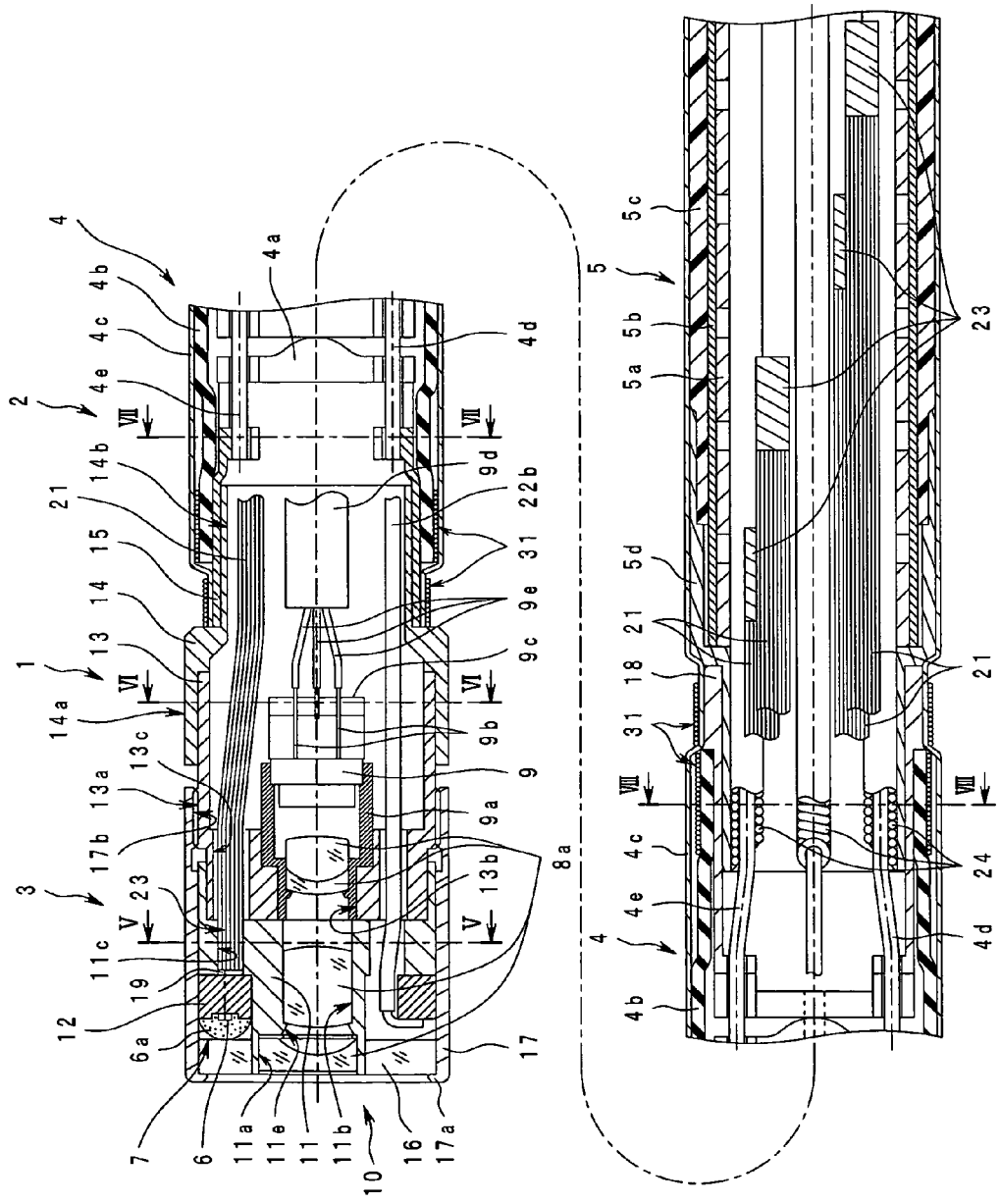
FIG. 2 is a sectional view at the line II-II of FIG. 1.

As shown in FIG. 2, an endoscope 1 according to the present embodiment has an elongated insertion unit 2. The insertion unit 2 includes a rigid distal end portion 3, a bending portion 4, and a flexible tube 5 which are connected in that order viewing from the distal end of the endoscope 1. The bending portion 4 includes a plurality of pieces connected to each other so that the portion 4 is bendable in the lateral and longitudinal directions. The flexible tube 5 is made of a flexible tubular member.

The distal end portion 3 has an LED illumination unit 7 and an observation optical unit 10. The LED illumination unit 7 includes a plurality of light emitting devices, such as light-emitting diode (LED) chips 6. The observation optical unit 10 includes a plurality of optical lenses 8a and a charge coupled device (CCD) 9.

The distal end portion 3 includes an objective optical system holder (hereinafter, abbreviated to the objective holder) 11, an LED substrate 12 for light emitting devices, a lens frame holder 13, a first connecting tube 14, a second connecting tube 15, a cover glass 16, and a connection fixing member 17.

Each of the objective holder 11 and the LED substrate 12 is made of a metal having a high thermal conductivity, such as copper or aluminum. On the other hand, each of the first connecting tube 14, the second connecting tube 15, and the connection fixing member 17, serving as the exteriors of the lens frame holder 13 and the endoscope 1, is made of a highly corrosion resistant metal having a low thermal conductivity, such as stainless steel.

Some of the optical lenses 8a, constituting the observation optical unit 10, are fixed in the objective holder 11 and the other optical lenses 8a and the CCD 9 are fixed in a lens frame 9a. Terminals 9b extending from the CCD 9 toward the proximal end of the endoscope 1 are electrically connected to a CCD substrate 9c. Signal lines 9e, passing through a signal cable 9d, are electrically connected to predetermined portions in the CCD substrate 9c.

The lens frame 9a is made of a highly corrosion resistant metal having a low thermal conductivity, such as stainless steel.

Figure 3:
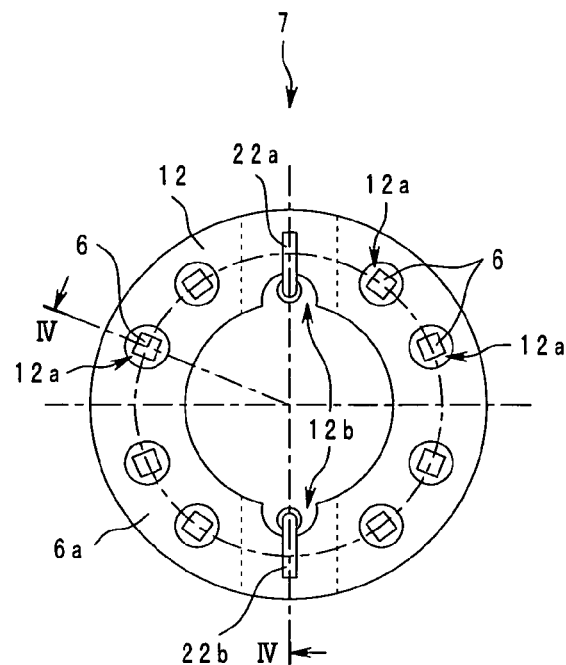
FIG. 3 is a diagram explaining an example of the arrangement of LED chips on an LED substrate.
Figure 4:
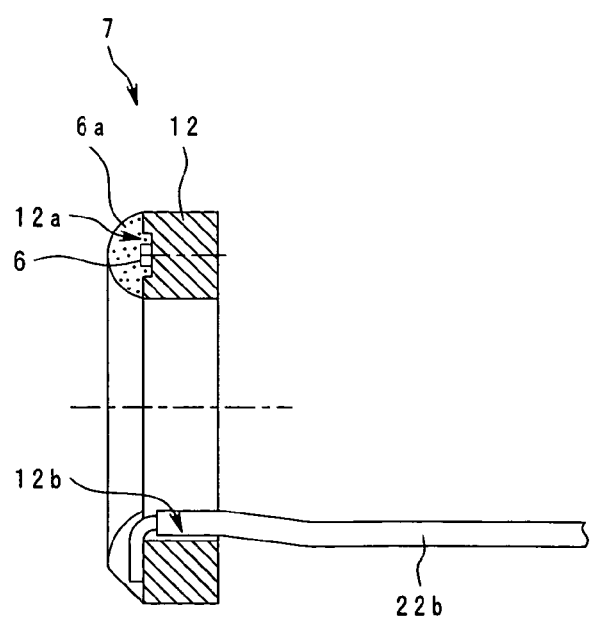
FIG. 4 is a sectional view at the line IV-IV of FIG. 3.

Referring to FIGS. 2 to 4, the LED illumination unit 7 includes the LED chips 6 and the LED substrate 12. The LED substrate 12 is ring-shaped and has, e.g., eight counterbored holes 12a which are formed at regular intervals at a predetermined distance from the center of the ring. The LED chips 6 are disposed in the counterbored holes 12a, respectively. Each LED chip 6 in the radiation direction is covered with a translucent sealing compound 6a.

A pair of notches 12b is formed on the inner surface of the LED substrate 12 so as to accommodate power cables 22a and 22b for power supply. In addition, the LED substrate 12 has a conductive pattern (not shown) that electric contacts (not shown) of the power cables 22a and 22b and the LED chips 6 are in electric contact with.

Figure 5:
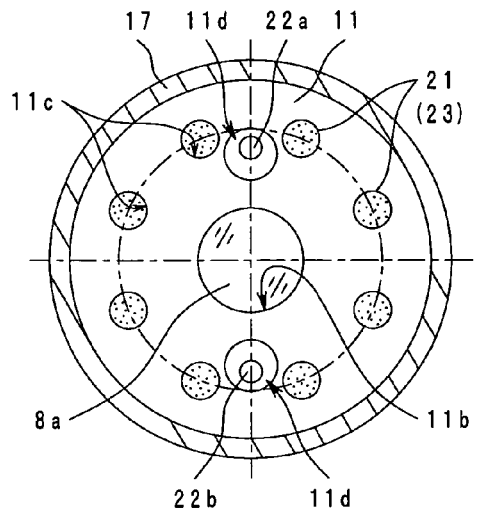
FIG. 5 is a sectional view at the line V-V of FIG. 2.

Referring to FIGS. 2 and 5, the objective holder 11 is substantially cylindrical. On the inner surface of the objective holder 11, recesses 11a and 11b are formed to accommodate the optical lenses 8a of the observation optical unit 10. The recess 11a is adjacent to the distal end of the objective holder 11 and the other recess 11b is adjacent to the proximal end thereof.

Heat-radiating member accommodation holes 11c are formed around the recess 11b at regular intervals such that the holes correspond to the respective counterbored holes 12a. The number of holes 11c is predetermined. In each hole 11c, a bundle member 21 is arranged. Each bundle member 21 serves as a heat-radiating member for radiating heat generated from the corresponding LED chip 6. In addition, a pair of holes 11d is formed in predetermined positions around the recess 11b such that the power cables 22a and 22b pass through the holes 11d, respectively.

Each bundle member 21 is formed in consideration of flexibility by making a plurality of wires 21a into a bundle. Each wire 21a is made of a metal having a high thermal conductivity, such as copper, aluminum, or silver. The diameter of each wire 21a is 0.1 mm or smaller. The number of wires 21a and the length of each wire 21a are properly set in consideration of heat capacity and workability depending on the type of endoscope.

In consideration of the workability, each end of each bundle member 21 is formed as a united portion 23 by, e.g., soldering or hard soldering, or using adhesive. According to the present embodiment, the number of united portions 23 arranged at the distal end of the endoscope 1 is eight. The surface at the distal end of each united portion 23 is flattened by polishing. On the other hand, the number of united portions 23 arranged adjacent to the proximal end of the endoscope 1 is four.

The recesses 11a and 11b are in communication with each other through a tapered hole 11e. The diameter of the tapered hole 11e adjacent to the distal end of the endoscope 1 is larger than that adjacent to the proximal end.

Figure 6:
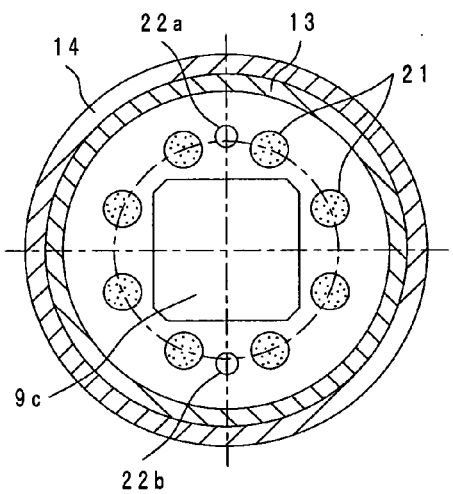
FIG. 6 is a sectional view at the line VI-VI of FIG. 2.

As shown in FIGS. 2 and 6, the lens frame holder 13 is substantially cylindrical. On the outer surface of the lens frame holder 13, an external thread segment 13a is formed in a predetermined position. The external thread segment 13a is screwed into an internal thread segment (17b in FIG. 2), which will be described below, formed in the connection fixing member 17. A through-hole 13b for the lens frame 9a, which constitutes the observation optical unit 10, is formed in the center of the lens frame holder 13 in the distal end portion thereof. In addition, heat-radiating member accommodation holes 13c are formed around the through-hole 13b such that the holes 13c correspond to the holes 11c, respectively. Each bundle member 21 is loosely fitted into the corresponding hole 13c.

The first connecting tube 14 includes a large-diameter portion 14a and a small-diameter portion 14b. The lens frame holder 13 is integrated with the second connecting tube 15. Specifically, the proximal end of the lens frame holder 13 is fitted into the distal inner surface of the large-diameter portion 14a of the first connecting tube 14. The outer surface of the small-diameter portion 14b is fitted into the distal inner surface of the second connecting tube 15.

The second connecting tube 15 is substantially tubular. The first connecting tube 14 and the bending portion 4 are integrally fitted into the second connecting tube 15. Specifically, the outer surface of the small-diameter portion 14b of the first connecting tube 14 is arranged on the distal inner surface of the second connecting tube 15. A distal-end bending piece 4a, a bending rubber 4b, and an external blade 4c constituting the bending portion 4 are arranged in predetermined positions in the proximal end portion of the second connecting tube 15. The bending rubber 4b and the external blade 4c are integrally fixed to the second connecting tube 15 by winding fixing members 31.

Figure 7:
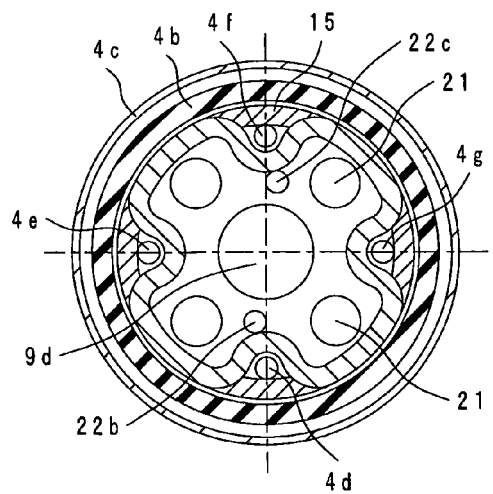
FIG. 7 is a sectional view at the line VII-VII of FIG. 2.

Referring to FIG. 7, a downward bending wire 4d, a leftward bending wire 4e, an upward bending wire 4f, and a rightward bending wire 4g are arranged in the bending portion 4.

Figure 1:
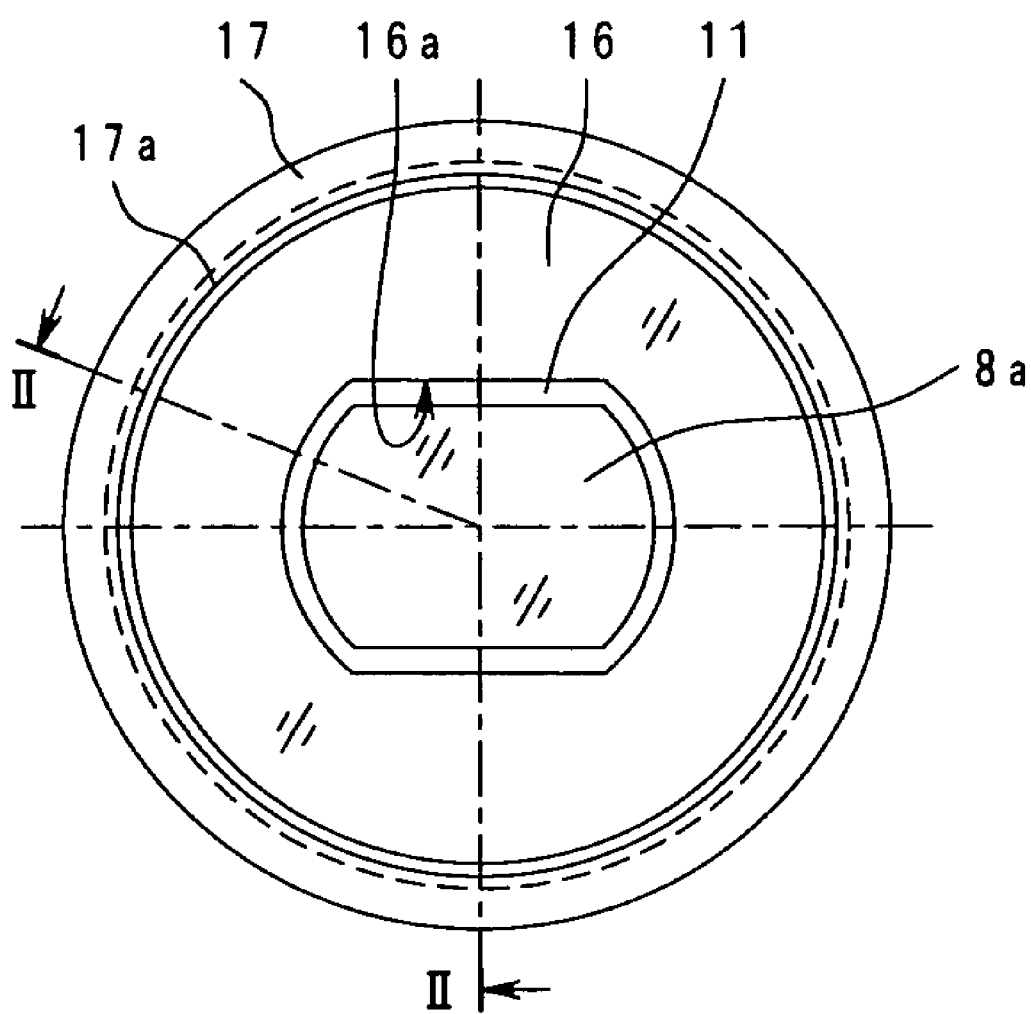
FIG. 1 is a front view of the distal end of an insertion unit according to a first embodiment of the present invention.

As shown in FIGS. 1 and 2, the cover glass 16 is made of, e.g., a substantially ring-shaped flat optical member. A through-hole 16a corresponding to the distal end of the objective holder 11 is formed in the center of the cover glass 16.

The connection fixing member 17 is substantially tubular. A fit portion 17a is formed on the inner circumference at the distal end of the connection fixing member 17. The fit portion 17a is in contact with the distal end of the cover glass 16. An internal thread segment 17b is formed in the proximal end portion of the connection fixing member 17 such that the external thread segment 13a formed in the lens frame holder 13 is screwed into the internal thread segment 17b.

Figure 8:
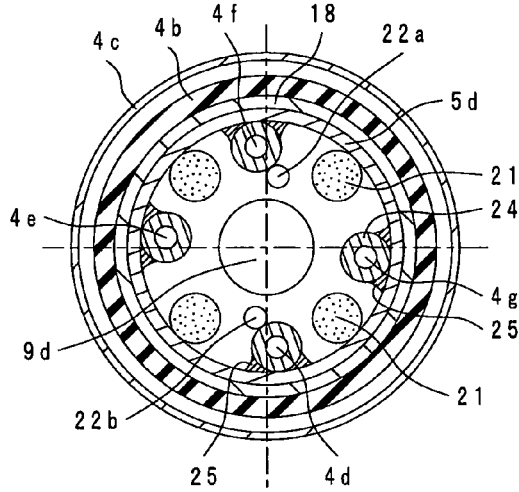
FIG. 8 is a sectional view at the line VIII-VIII of FIG. 2.

Referring to FIGS. 2, 7, and 8, the eight bundle members 21 respectively extend to the proximal end of the endoscope 1 through the holes 11c, the objective holder 11, the first connecting tube 14, and the second connecting tube 15. In order to be appropriate to the bending direction and a space in the pieces 4a, the eight bundle members 21 are combined into four bundle members 21 in the vicinity of the bending portion 4 such that two adjacent bundle members 21 are combined into one bundle. The four bundle members 21 extending through the bending portion 4 are arranged in the flexible tube 5. The four bundle members 21 in the flexible tube 5 have different lengths. Therefore, the respective united portions 23 of the four bundle members 21 are arranged in different positions in the flexible tube 5.

The flexible tube 5 includes a spiral tube 5a arranged on the inner surface of the tube 5, a mesh tube 5b covering the spiral tube 5a, and an external tube 5c covering the mesh tube 5b. The flexible tube 5 further includes a distal connector 5d at the distal end. The distal connector 5d is arranged on the inner surface of a third connecting tube 18 that constitutes the proximal part of the bending portion 4. Each of the bending wires 4d to 4g is extended through a coil component 24. The coil components 24 are integrally joined to predetermined portions on the inner surface of the distal connector 5d by brazing 25.

Figure 9:
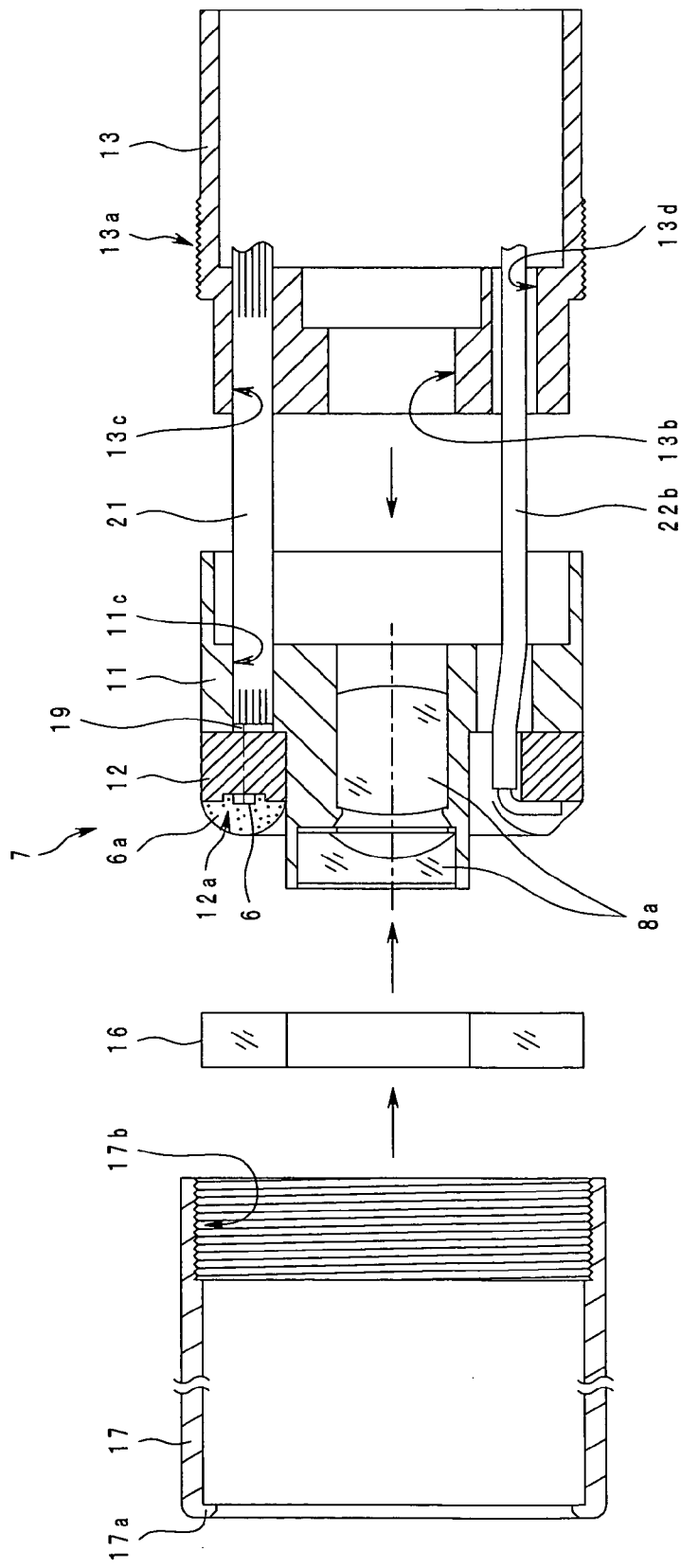
FIG. 9 is a diagram explaining a process of assembling a distal end portion.

A process of assembling the distal end portion 3 will now be described with reference to FIG. 9.

First, silicone grease 19 having a high thermal conductivity is applied to the inner surface of the LED substrate 12 constituting the LED illumination unit 7. In this state, the objective holder 11 in which the optical lenses 8a are disposed is come into contact with the inner surface of the LED substrate 12. After that, the united portions 23, serving as the distal ends of the bundle members 21 each including the predetermined number of wires 21a, are arranged in the holes 11c in the objective holder 11, respectively. In this instance, the distal end of each united portion 23 is closely attached to the proximal surface of the LED substrate 12, with the silicone grease 19 therebetween. The united portions 23 are fixed to the LED substrate 12 by soldering. The power cables 22a and 22b extending from the LED substrate 12 are arranged in the notches 12b, respectively.

Thus, the LED substrate 12 is in tight contact with the objective holder 11, with the silicone grease 19 therebetween. In addition, the bundle members 21 are arranged in tight contact with the objective holder 11 by soldering.

Instead of the silicone grease 19, a high-thermal-conductivity filler, a heat transfer sheet, or a heat transfer film may be used.

Subsequently, the cover glass 16 is attached to the distal-end surface of the LED substrate 12. The distal end of the lens frame holder 13 is inserted into a recess at the proximal end of the objective holder 11. In this instance, the bundle members 21 are inserted into the holes 13c, respectively.

Subsequently, the cover glass 16, the LED substrate 12, and the objective holder 11 are capped on their circumferences with the connection fixing member 17 in that order. Then, the distal end of the connection fixing member 17 reaches the vicinity of the external thread segment 13a formed at the lens frame holder 13. In this instance, the external thread segment 13a is screwed into the internal thread segment 17b formed at the connection fixing member 17. Thus, the connection fixing member 17 is fixed to the lens frame holder 13 in a predetermined screwed state.

Thus, the cover glass 16 is come into tight contact with the sealing compound 6a by a predetermined pressure and the LED substrate 12 is come into tight contact with the objective holder 11 by a predetermined pressure, so that they are assembled into one unit.

After that, the lens frame 9a including the CCD 9 is fixed to this unit and the unit is connected to the bending portion 4 through the first connecting tube 14 and the second connecting tube 15. In this manner, the endoscope 1 is formed.

The operation of the endoscope 1 with the above-described structure will now be explained.

First, the LED illumination unit 7 is supplied with power through the power cables 22a and 22b, so that the LED chips 6 arranged in the LED substrate 12 emit light. Thus, an observation area is illuminated by light. An optical image of the illuminated observation area is formed on the surface of the CCD 9 through the optical lenses 8a of the observation optical unit 10, thus obtaining an endoscopic image.

While endoscopic images are being observed, the insertion unit 2 of the endoscope 1 is moved to a target observation area. In this instance, the bending portion 4 is bent in a desired direction by appropriately manipulating bending-portion operating means (not shown). In the bending portion 4, the flexible bundle members 21 are extendedly arranged separately in consideration of the bending direction. Accordingly, the bending portion 4 is easily bendable.

The LED illumination unit 7 is continuously supplied with power, so that heat generated from the LED chips 6 is gradually transferred to the LED substrate 12. Thus, the temperature of the LED substrate 12 gradually increases. The heat transferred through the LED substrate 12 is further transferred to the bundle members 21 which are in tight contact with the rear of the LED substrate 12, with the silicone grease 19 therebetween. The heat is also transferred to the objective holder 11 arranged on the rear of the LED substrate 12.

The heat transmitted through the objective holder 11 is transferred to the sides of the bundle members 21, the sides being joined to the inner surfaces of the holes 11c formed at the objective holder 11 by soldering, respectively. Each bundle member 21 conducts the heat from the distal end thereof in the direction toward the proximal end.

As mentioned above, the heat generated by the LED chips is transmitted from the distal ends of the elongated bundle members in the direction toward the proximal ends through the LED substrate and the objective holder. Advantageously, the LED illumination unit can be prevented from being heated at a high temperature. In addition, the conduction of heat generated by the LED chips to the CCD can be prevented with reliability.

Consequently, an observation area is illuminated by the desired amount of light for a long time to obtain good endoscopic images without noises, so that endoscopic observation can be performed using the images.

Figure 10:
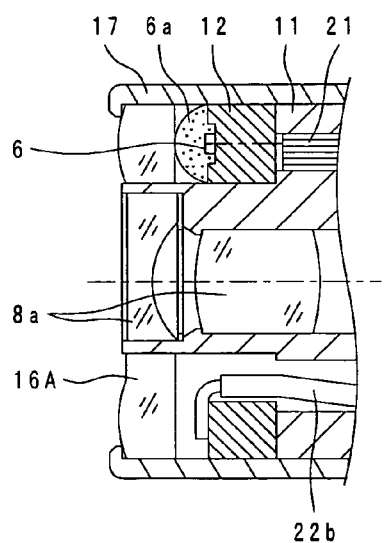
FIG. 10 is a diagram showing the distal end portion with a cover glass having a convex distal-end surface.
Figure 11:
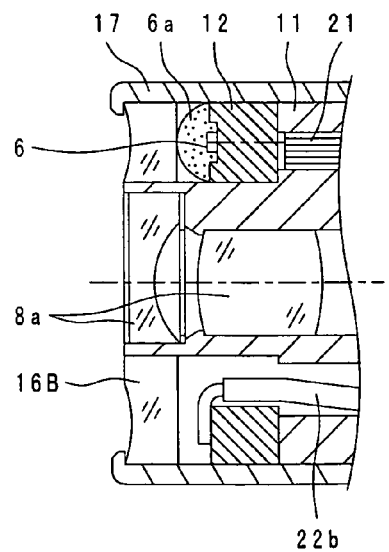
FIG. 11 is a diagram showing the distal end portion with a cover glass having a concave distal-end surface.

According to the present embodiment, the cover glass 16 is made of a flat optical member. The cover glass is not limited to that type. For example, a cover glass 16A having a convex distal-end surface as shown in FIG. 10 or a cover glass 16B having a concave distal-end surface as shown in FIG. 11 may be used.

In addition, the LED substrate 12 can be integrated with the objective holder 11.

Figure 12:
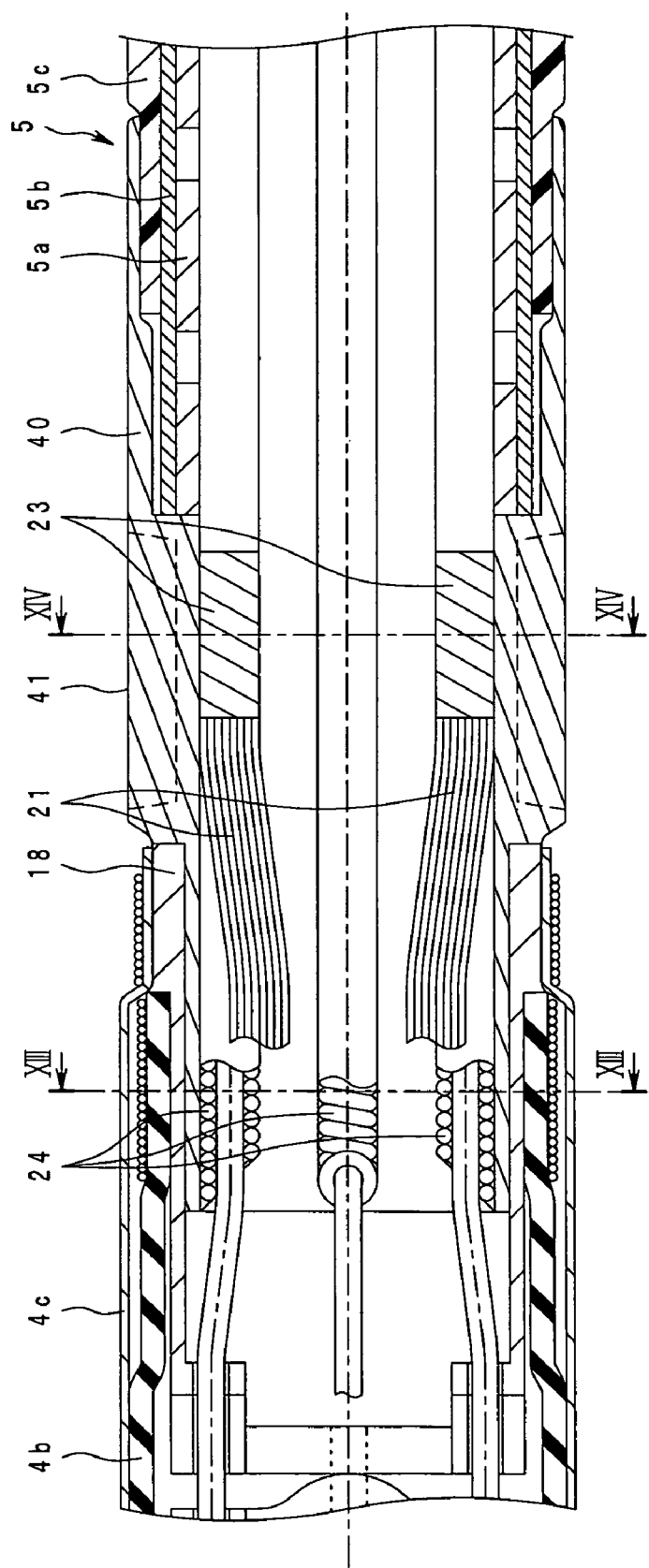
FIG. 12 is a sectional view explaining the structures of bundle members in the vicinity of a distal connector, the proximal end portion of each bundle member constituting a united portion joined to the distal connector.
Figure 13:
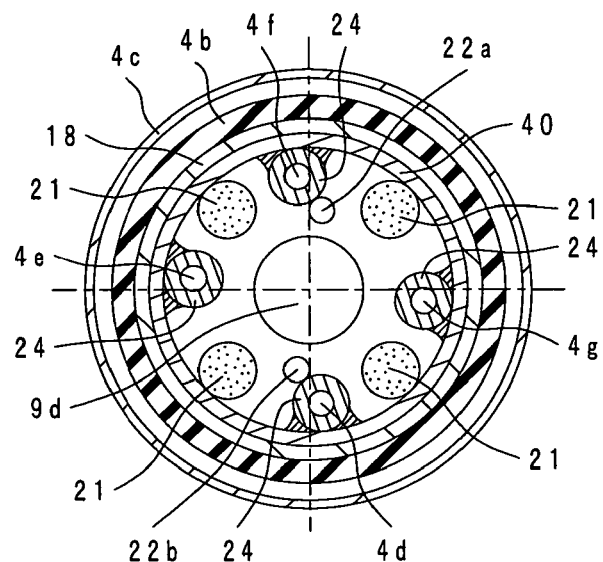
FIG. 13 is a sectional view at the line XIII-XIII of FIG. 12.
Figure 14:
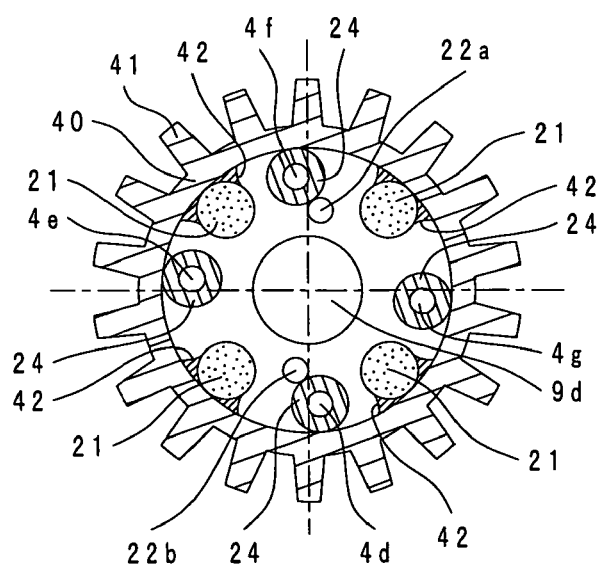
FIG. 14 is a sectional view at the line XIV-XIV of FIG. 12.
Figure 15:
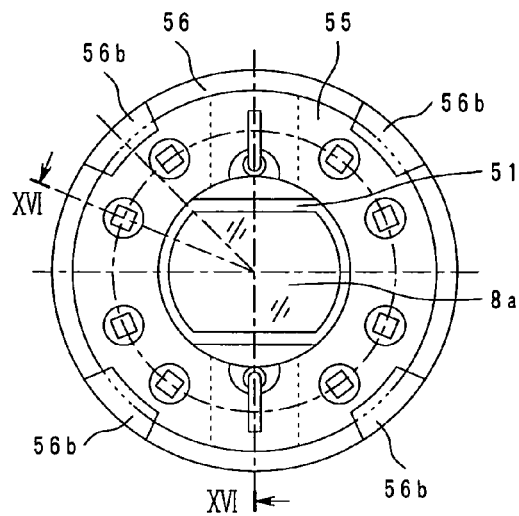
FIG. 15 is a front view of the distal end of an insertion unit according to a second embodiment of the present invention.
Figure 17:
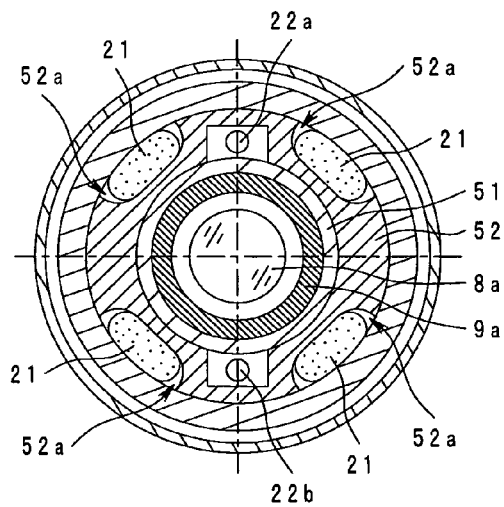
FIG. 17 is a sectional view at the line XVII-XVII of FIG. 16.
Figure 18:
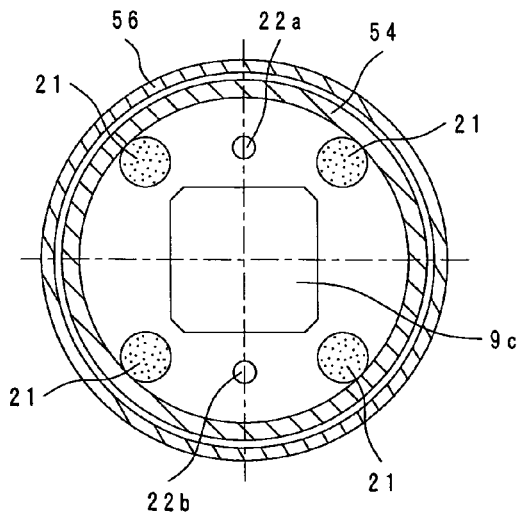
FIG. 18 is a sectional view at the line XVIII-XVIII of FIG. 16.
Figure 16:
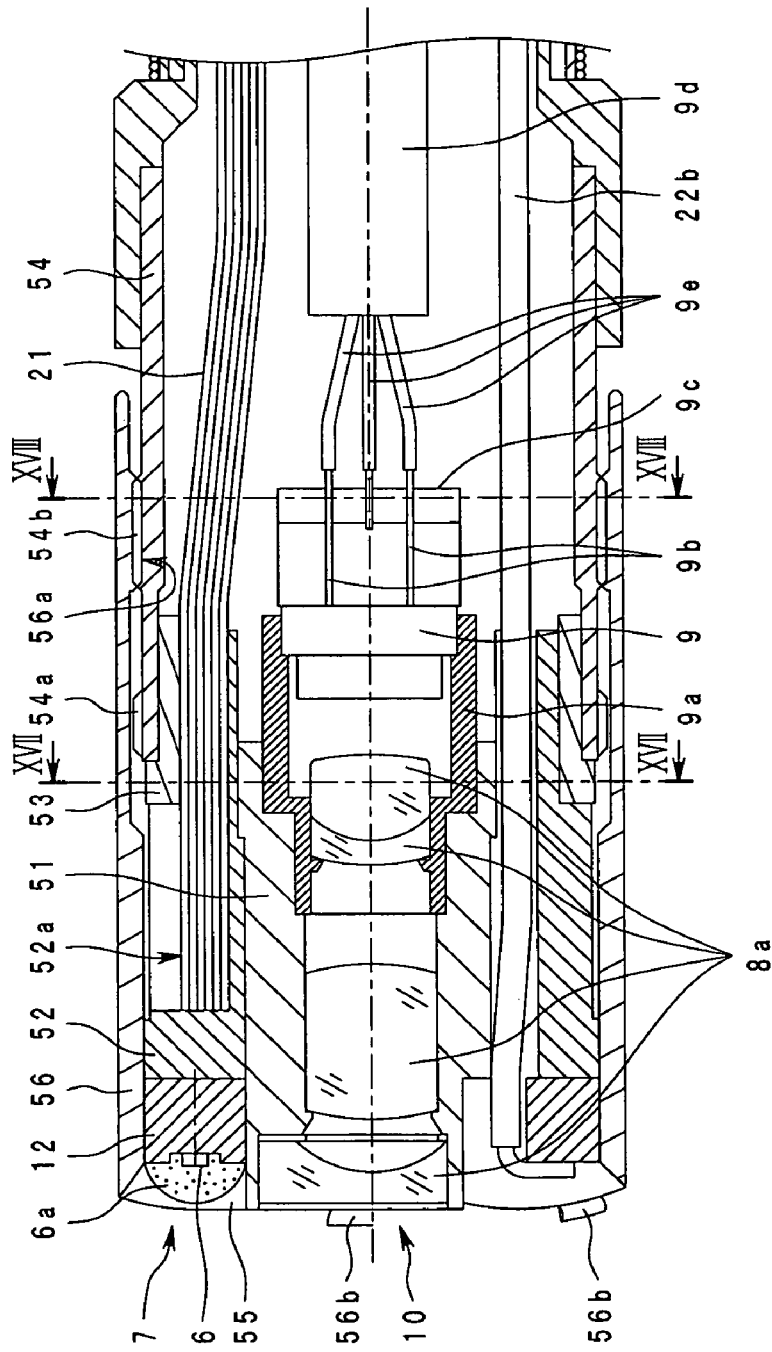
FIG. 16 is a sectional view at the line XVI-XVI of FIG. 15.
Figure 19:
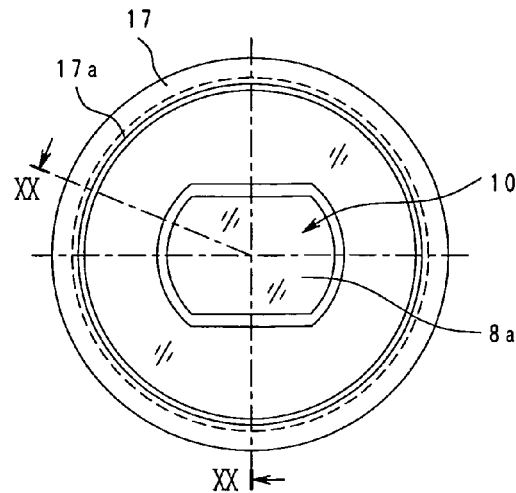
FIG. 19 is a front view of the distal end of an insertion unit of a rigid endoscope according to a third embodiment of the present invention.
Figure 21:
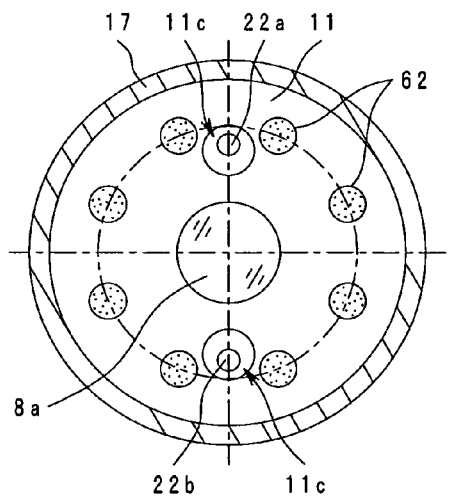
FIG. 21 is a sectional view at the line XXI-XXI of FIG. 20.
Figure 22:
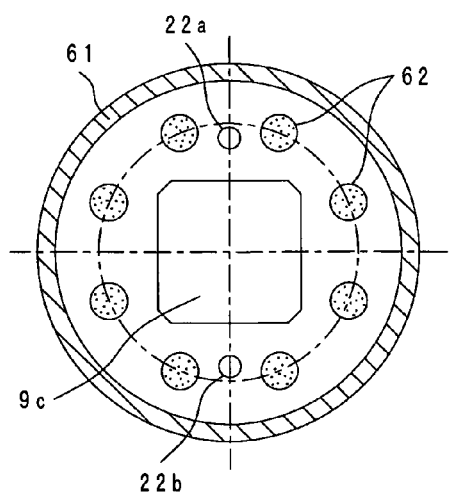
FIG. 22 is a sectional view at the line XXII-XXII of FIG. 20.

Instead of the arrangement of the proximal ends of the bundle members 21 in the flexible tube 5, as shown in FIGS. 12 to 14, the united portions 23 of the bundle members 21 may be joined to predetermined portions on the inner surface of a distal connector 40 using a joining material such as solder 42. The distal connector 40 has a cooling fin 41 on the outer surface.

Consequently, heat conducted through the bundle members 21 can be efficiently radiated from the distal connector 40, thus remarkably increasing the radiation effect of the bundle members 21.

In addition, each bundle member 21 may include a stranded wire or a wire mesh.

A second embodiment of the present invention will be described below with reference to FIGS. 15 to 18.

The objective holder 11 according to the first embodiment is made of a metal having a high thermal conductivity, such as copper or aluminum. According to the second embodiment, an objective holder dividingly includes an objective frame 51 made of a metal having a low thermal conductivity and an LED holder 52 made of a metal having a high thermal conductivity.

A ring member 53 is arranged at the proximal end of the LED holder 52. A tubular fixing member 54 is arranged on the outer surface of the ring member 53.

According to the second embodiment, a covering member 55 for further covering a sealing compound 6a overlaid on LED chips 6 is used instead of a cover glass.

Four notches 52a are formed in predetermined positions on the outer surface of the LED holder 52 to accommodate bundle members 21.

First and second external thread segments 54a and 54b, serving as a dual thread, are formed in predetermined positions on the outer surface of the tubular fixing member 54. The external thread segments 54a and 54b are screwed into an internal thread segment 56a formed in the proximal end portion of a connection fixing member 56 that is substantially tubular. Projections 56b are formed at the distal end of the connection fixing member 56 so that the projections 56b are come into contact with the covering member 55.

A process of assembling a distal end portion 3 will now be described.

First, silicone grease having a high thermal conductivity is applied to the proximal surface of an LED substrate 12 constituting an LED illumination unit 7. In this state, the objective frame 51 and the LED holder 52 in which optical lenses 8a are disposed are arranged in predetermined positions. After that, the four bundle members 21 are arranged in the notches 52a through-holes constituted of the LED holder 52 and the ring member 53. Solder or adhesive is supplied to openings of the notches 52a, thus fixing the bundle members 21 to the LED holder 52.

Thus, the LED substrate 12 is in tight contact with the objective frame 51, with the silicone grease therebetween. In addition, the bundle members 21 are arranged in tight contact with the LED holder 52, with, e.g., solder therebetween.

Subsequently, the tubular fixing member 54 is arranged on the outer surface of the ring member 53. The connection fixing member 56 caps the LED substrate 12, the LED holder 52, and the ring member 53 in that order. Then, the end of the connection fixing member 56 reaches the vicinity of the first external thread segment 54a formed at the tubular fixing member 54. In this instance, the first external thread segment 54a is screwed into the internal thread segment 56a formed at the connection fixing member 56.

After the internal thread segment 56a passes the first external thread segment 54a, the distal-end surface of the connection fixing member 56 reaches the vicinity of the second external thread segment 54b. Then, the second external thread segment 54b is screwed into the internal thread segment 56a. Thus, the connection fixing member 56 is fixed to the tubular fixing member 54.

Thus, the projections 56b of the connection fixing member 56 are come into contact with the covering member 55 by a predetermined pressure and the LED substrate 12, the LED holder 52, and the ring member 53 are come into contact with each other by a predetermined pressure, so that they are assembled into one unit.

After that, a lens frame 9a including a CCD 9 is joined to this unit and the unit is connected to a bending portion 4 through first and second connecting tubes 14 and 15. In this manner, an endoscope 1 according to the second embodiment is constructed.

Before the LED holder 52 is integrated with the objective frame 51, the lens frame 9a may be joined to the objective frame 51. The other structure and operation of the endoscope 1 according to the second embodiment are similar to those according to the first embodiment. The same components as those of the first embodiment are designated by the same reference numerals and a description thereof is omitted.

As mentioned above, the bundle members are arranged in the LED holder having the notches. In this state, the solder is supplied to the openings of the notches, thus joining integrally the bundle members to the LED holder. Accordingly, it is unnecessary to preliminarily process, e.g., flattening the distal-end surface of each bundle member. Advantageously, the workability can be improved.

In addition, the connection fixing member is fixed to the tubular fixing member by the double thread. Thus, the disconnection of the connection fixing member from the tubular fixing member can be prevented with higher reliability. Other advantages of the second embodiment are the same as those of the first embodiment.

The LED holder 52 may be integrated with the LED substrate 12.

A third embodiment of the present invention will now be described with reference to FIGS. 19 to 22.

The present embodiment relates to a rigid endoscope 60 including a rigid tube 61 instead of the foregoing bending portion 4. The rigid tube 61 has a predetermined length. The rigid endoscope 60 does not include the foregoing lens frame holder 13, first connecting tube 14, and second connecting tube 15. An external thread segment 61a formed in the distal end portion of the rigid tube 61 is screwed into an internal thread segment 17b of a connection fixing member 17, thus the rigid endoscope 60 being formed.

According to the third embodiment, instead of the bundle members 21, serving as heat-radiating members, elongated rod members 62 having a high thermal conductivity, made of copper, aluminum, silver, or carbon graphite, are arranged in predetermined positions. Each rod member 62 has a predetermined cross section and further has a predetermined length. The other structure of the rigid endoscope 60 is substantially the same as that of the endoscope 1 according to the first embodiment.

The rigid tube 61 has holes 61b for the rod members and a through-hole 61c for a lens frame.

In the above-described rigid endoscope having a rigid insertion unit, rigid heat-radiating members are arranged instead of flexible heat-radiating members to conduct heat generated by LED chips from the distal ends of the respective rod members in the direction toward the proximal ends via an LED substrate and an objective holder, thus preventing an LED illumination unit from being heated at a high temperature. In addition, the heat generated from the LED chips can be prevented from being transferred to a CCD with reliability.

Figure 23:
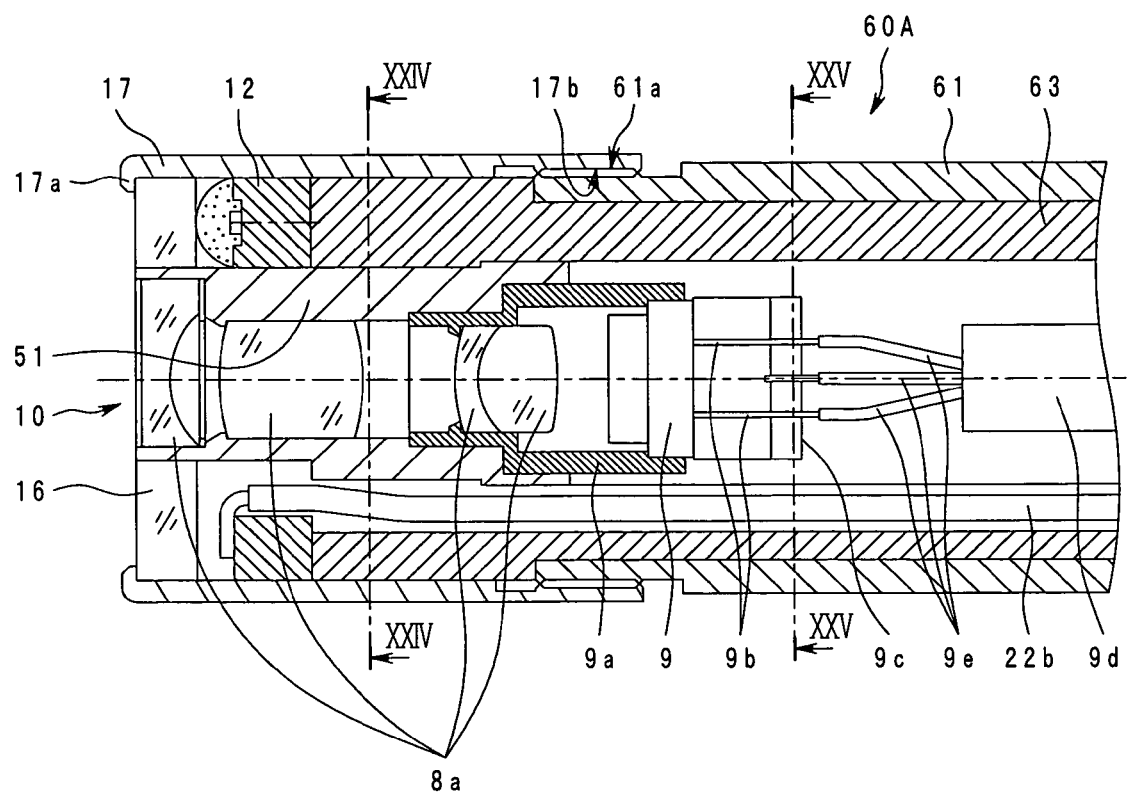
FIG. 23 is a longitudinal sectional view showing the structure of a rigid endoscope according to a modification of the third embodiment.
Figure 24:
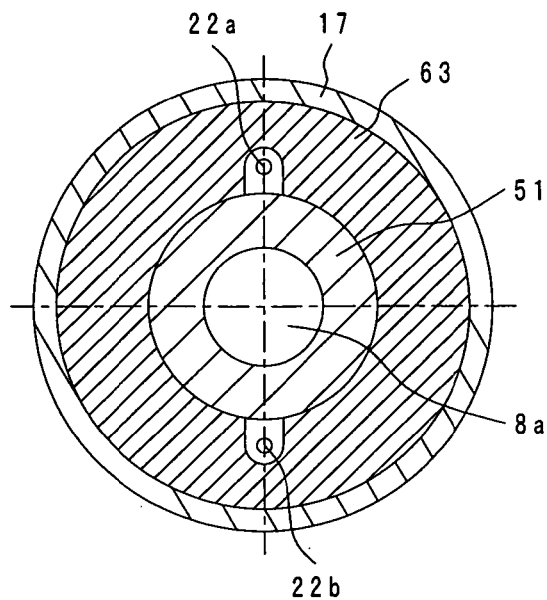
FIG. 24 is a sectional view at the line XXIV-XXIV of FIG. 23.
Figure 25:
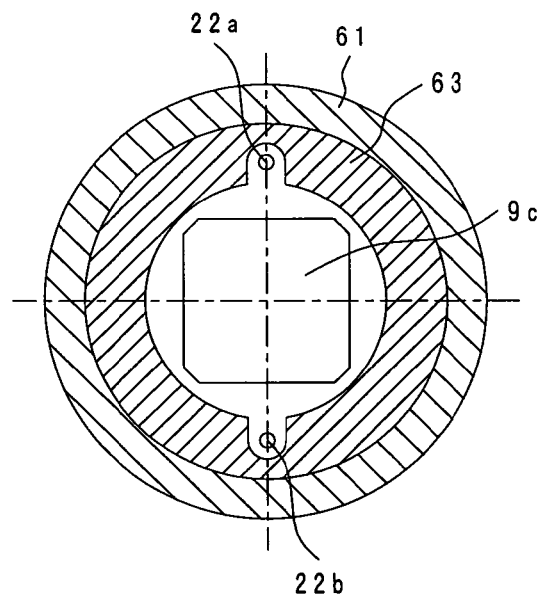
FIG. 25 is a sectional view at the line XXV-XXV of FIG. 23.

FIGS. 23 to 25 are diagrams explaining the structure of another rigid endoscope according to a modification of the second embodiment. As shown in the diagrams, a rigid endoscope 60A may include an objective frame 51 that is similar to that shown in FIGS. 15 to 17 and an elongated LED holder 63 that is substantially tubular and has a predetermined length.

Thus, the same operation and advantages as those of the second embodiment can be obtained.

A fourth embodiment of the present invention will now be described with reference to FIGS. 26 to 55.

Figure 26:
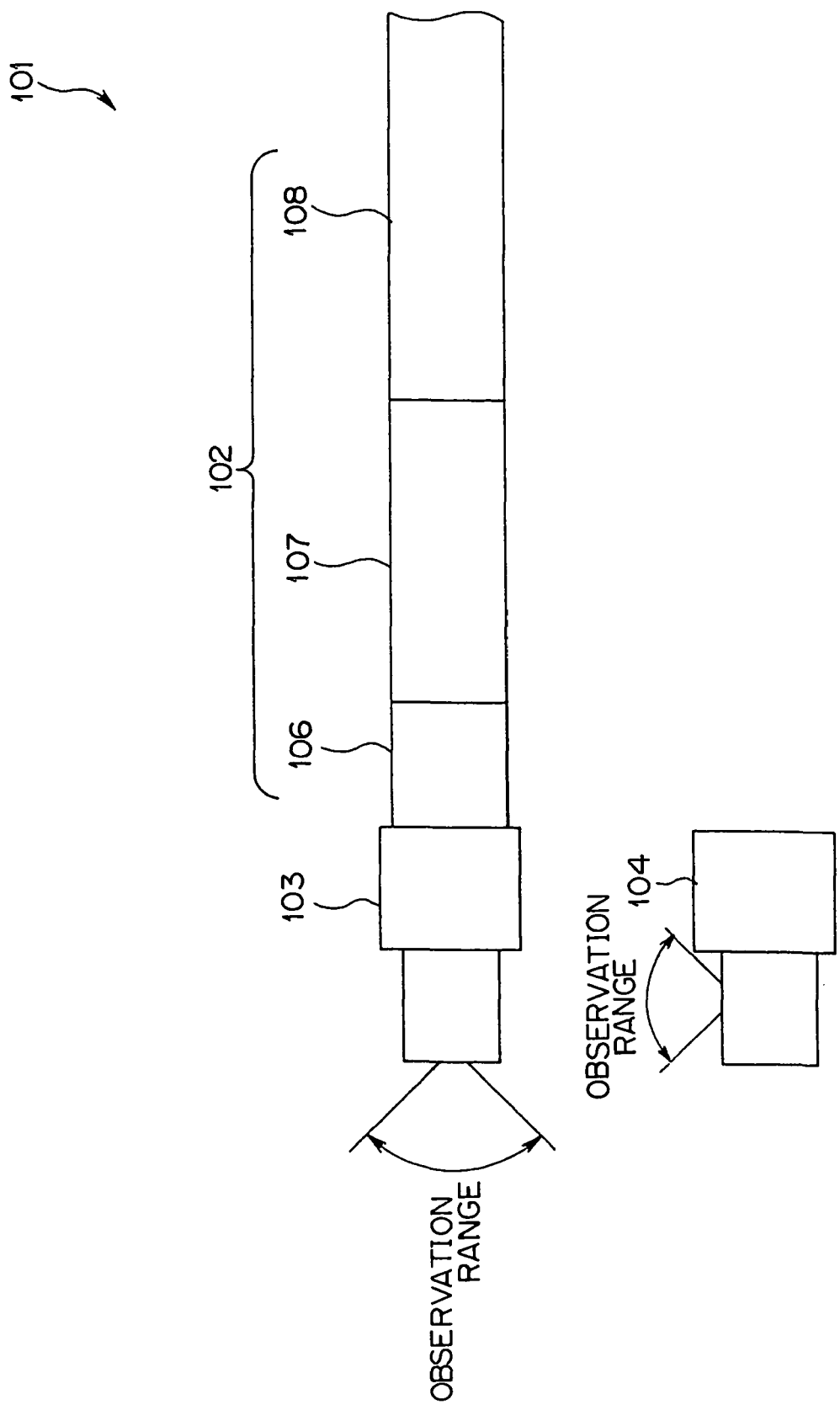
FIG. 26 is a diagram explaining the relationship between an insertion unit and a distal-end adapter according to a fourth embodiment of the present invention, two types of distal-end adapters being shown.
Figure 27:
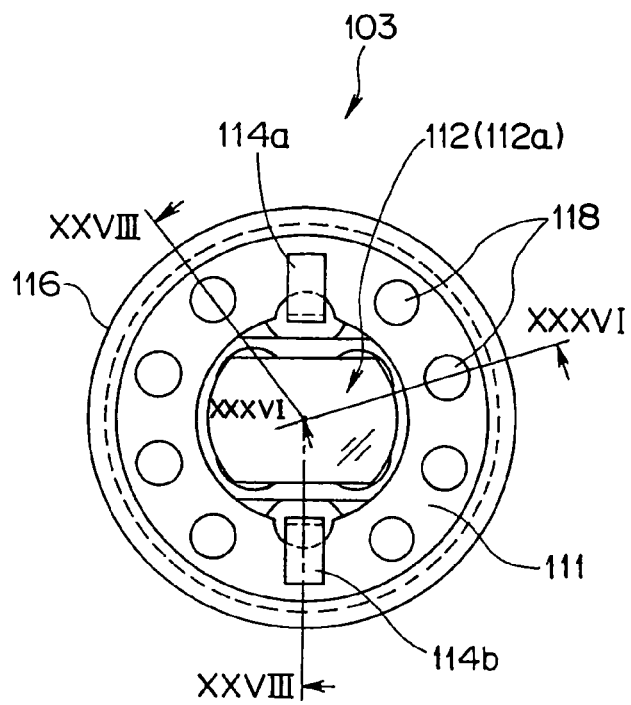
FIG. 27 is a front view of a direct-view type distal-end adapter.
Figure 28:
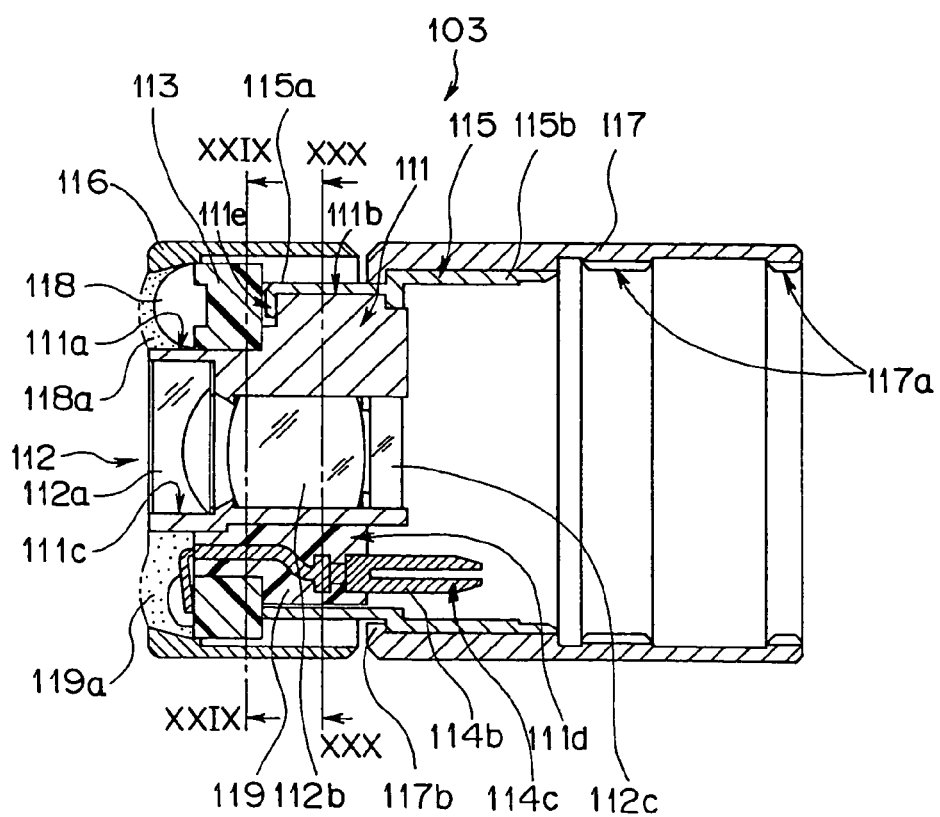
FIG. 28 is a sectional view at the line XXVIII-XXVIII of FIG. 27.
Figure 29:
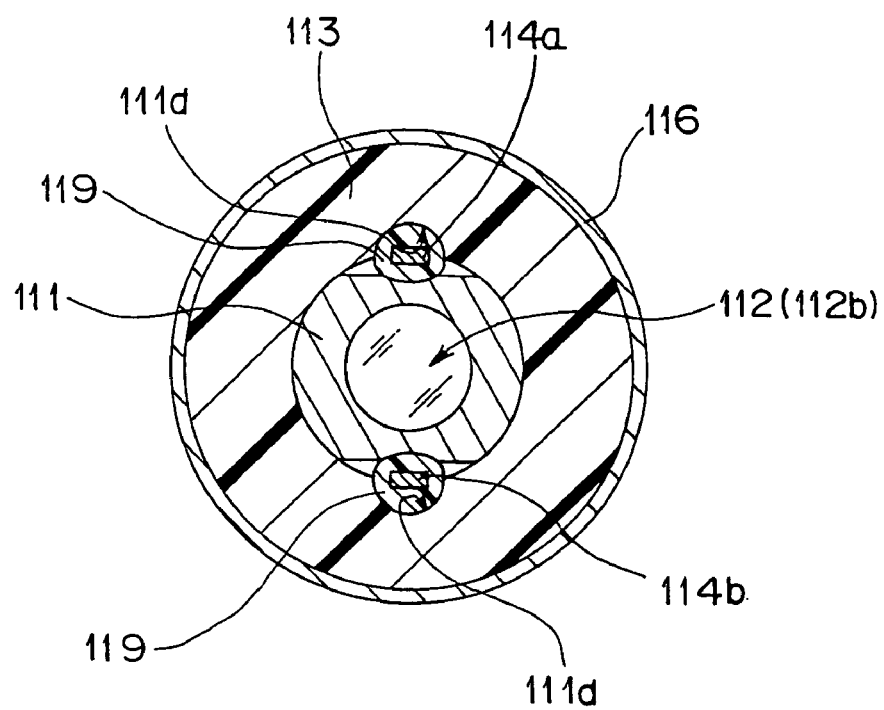
FIG. 29 is a sectional view at the line XXIX-XXIX of FIG. 28.
Figure 30:
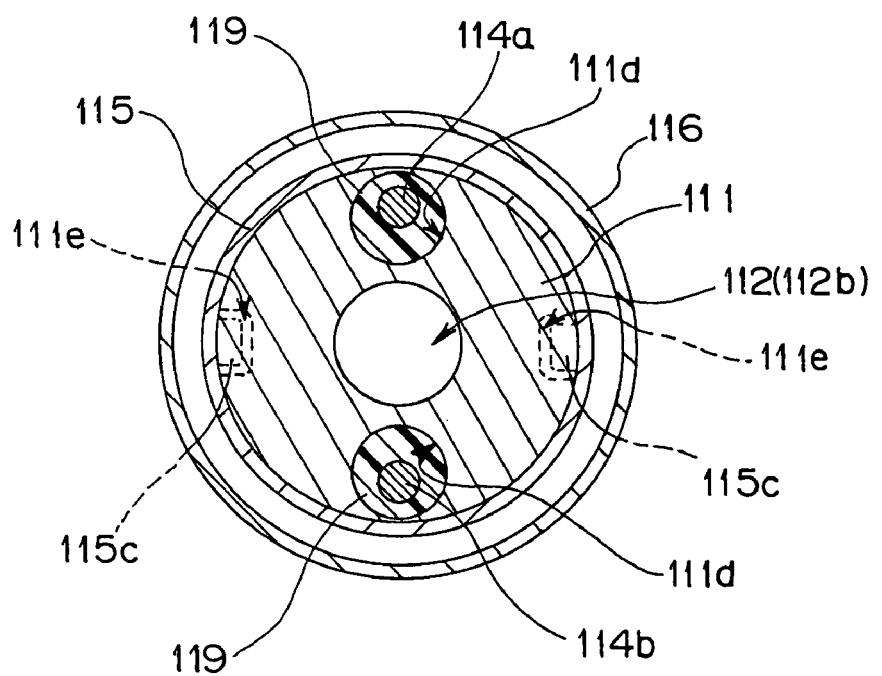
FIG. 30 is a sectional view at the line XXX-XXX of FIG. 28.
Figure 31:
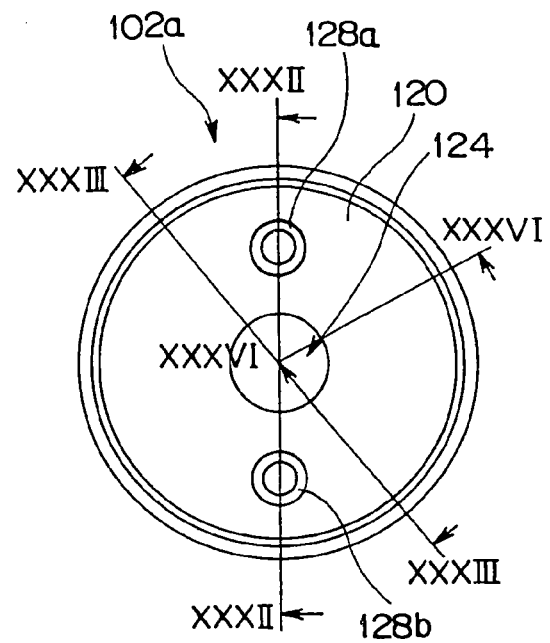
FIG. 31 is a front view of the insertion unit of the endoscope.
Figure 33:
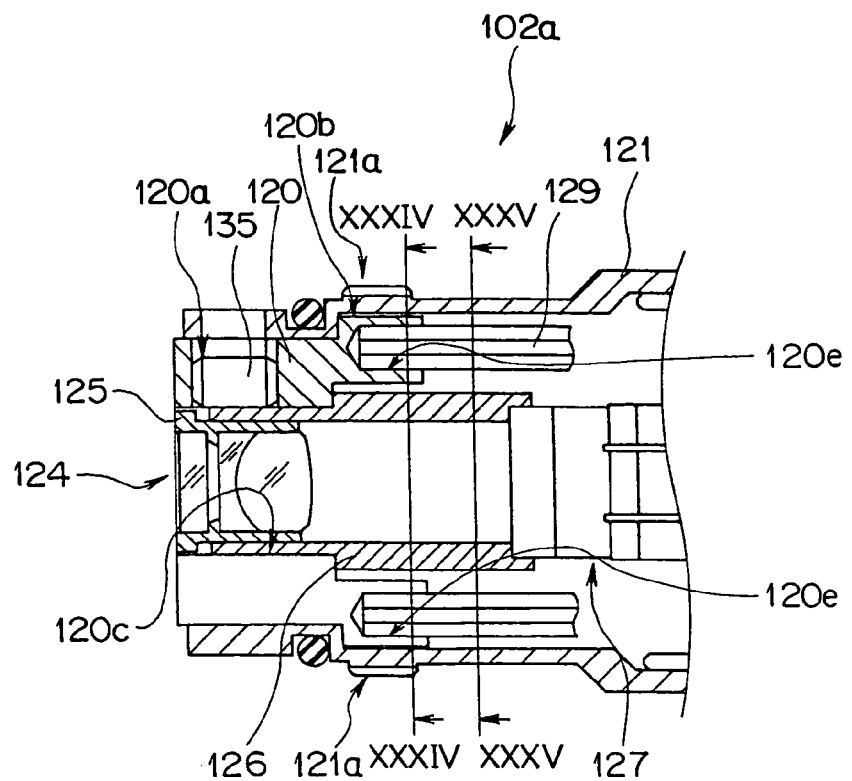
FIG. 33 is a sectional view at the line XXXIII-XXXIII of FIG. 31.
Figure 34:
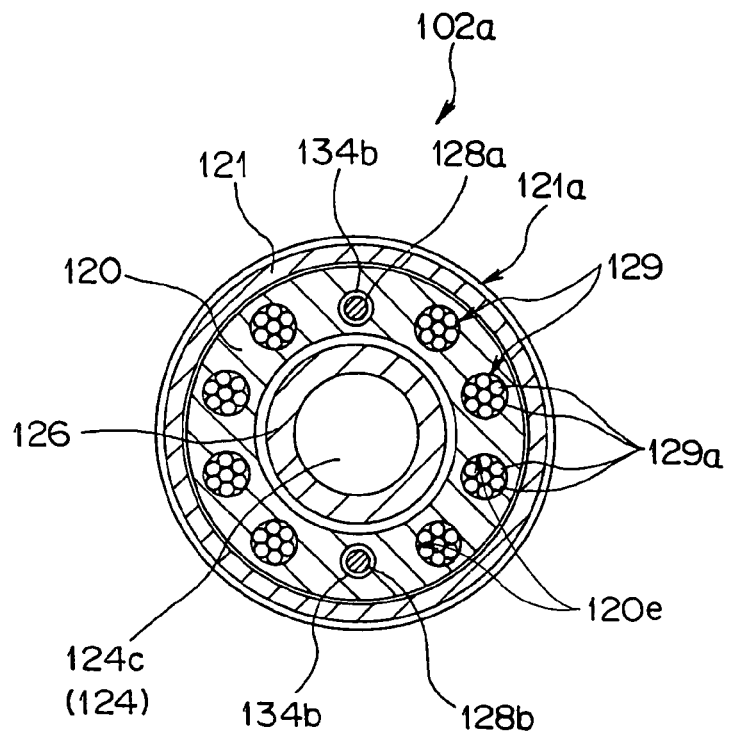
FIG. 34 is a sectional view at the line XXXIV-XXXIV of FIG. 33.
Figure 35:
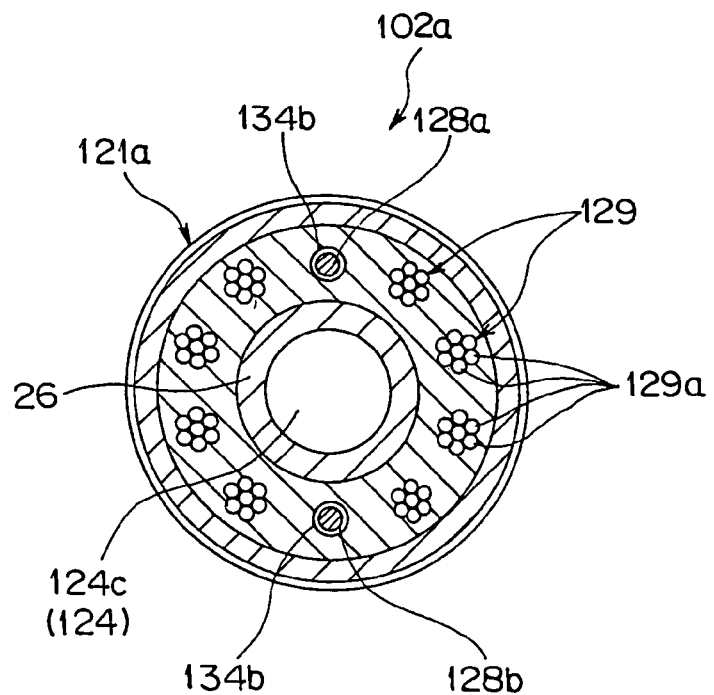
FIG. 35 is a sectional view at the line XXXV-XXXV of FIG. 33.

As shown in FIG. 26, an endoscope 101 according to the present embodiment has an elongated insertion unit 102. The insertion unit 102 includes a rigid distal end portion 106, a bending portion 107, and a flexible tube 108 connected in that order from the distal end. The bending portion 107 includes a plurality of bent pieces connected such that the bending portion 107 is bendable in the lateral and longitudinal directions. The flexible tube 108 is made of a flexible tubular member.

A direct-view type distal-end adapter 103, a side-view type distal-end adapter 104 or the like is selectively attachable to the distal end portion 106. The direct-view type distal-end adapter 103 includes a direct-view objective optical system, of which the range of observation is set in the longitudinal direction of the insertion unit. The side-view type distal-end adapter 104 includes a side-view objective optical system, of which the range of observation is set in the direction perpendicular to the longitudinal direction of the insertion unit.

The structure of the direct-view type distal-end adapter 103 will now be described with reference to FIGS. 27 to 30.

The direct-view type distal-end adapter 103 includes an adapter body 111, an objective optical unit 112, an LED substrate 113, adapter terminals 114, an adapter-body support member 115, a cover member 116, and an adapter release ring member (hereinafter, abbreviated to a ring member) 117.

The adapter body 111 is a first heat-radiating member made of a metal having a high thermal conductivity, such as copper or aluminum. The adapter body 111 is tubular and has a substantially convex cross section. In other words, the adapter body 111 includes a small-diameter portion 111a and a large-diameter portion 111b. In addition, a stepped central through-bore 111c is formed to substantially the center of the adapter body 111 in the longitudinal direction. A pair of holes 111*d* for accommodating the adapter terminals 114 is further formed in the adapter body 111.

The objective optical unit 112 includes optical lenses 112*a* to 112*c* arranged in the central through-bore 111*c*.

The LED substrate 113 is composed of, e.g., an aluminum circular plate having a central through-hole. A conductive pattern (not shown) is formed on one surface of the LED substrate 113. A plurality of LED illumination lights 118, serving as light emitting devices, and the one ends of the adapter terminals 114 are arranged in the conductive pattern. The LED substrate 113 is substantially in tight contact with the small-diameter portion 111*a*. The LED illumination lights 118, e.g., eight LED illumination lights 118 are arranged at regular intervals on a circumference at a predetermined distance from the center of the LED substrate 113. The LED illumination lights 118 in the radiation direction are covered with a translucent sealing compound 118*a*.

The adapter terminals 114 are one pair of metallic components constituting a first electric connecting unit. The one ends of the adapter terminals 114 are electrically connected to the conductive pattern. The other end of each adapter terminal 114 has a notch and functions as an elastic contact 114*c*. Each elastic contact 114*c* protrudes substantially perpendicularly with respect to the other surface of the LED substrate 113. One of the adapter terminals 114, i.e., an adapter terminal 114*a* serves as a power supply terminal. The other adapter terminal, i.e., an adapter terminal 114*b* serves as a ground terminal.

The adapter-body support member 115 is a stepped tubular member including a small-diameter portion 115*a* and a large-diameter portion 115*b*. The small-diameter portion 115*a* is arranged on the large-diameter portion 111*b*. The small-diameter portion 115*a* has embosses 115*c* at one end. The large-diameter portion 111*b* has recesses 111*e* corresponding to the embosses 115*c*. In other words, the embosses 115*c* are fitted into the recesses 111*e*, so that the adapter-body support member 115 is integrally attached to the adapter body 111.

The cover member 116 is a support member. Specifically, arranging the cover member 116 supports the LED substrate 113 on the adapter body 111.

The ring member 117 is freely rotatably arranged on the adapter-body support member 115. Internal thread segments 117*a* are formed on the inner surface of the ring member 117. The ring member 117 has a bent portion 117*b* that is come into contact with a step formed between the small-diameter portion 115*a* and the large-diameter portion 115*b* of the adapter-body support member 115.

Insulating sealing resins 119 and 119*a* are used. The adapter holes 111*d* are filled with the sealing resin 119 such that the adapter terminals 114*a* and 114*b* are covered with the sealing resin 119. For this purpose, the adapter terminals 114 and the sealing resin 119 are integrally formed by, e.g., insert molding.

The structure of the distal end portion of the insertion unit will now be described with reference to FIGS. 31 to 35.

The distal end portion 106 includes an objective optical system holder (hereinafter, abbreviated to an objective holder) 120, a first connecting tube 121, a second connecting tube 122, a third connecting tube 123, an observation optical unit 124, a lens frame 125, a main frame 126, an image pickup device 127, insertion-unit terminals 128, and bundle members 129.

The objective holder 120 is a second heat-radiating member made of a metal having a high thermal conductivity, such as copper or aluminum. The objective holder 120 is tubular and has a substantially convex cross section. In other words, the objective holder 120 includes a small-diameter portion 120*a* and a large-diameter portion 120*b*. In addition, a central through-hole 120*c* is formed in substantially the center of the objective holder 120 in the axial direction. A pair of holes 120*d* for insertion-unit terminals 128*a* and 128*b* is further formed at the objective holder 120. The insertion-unit terminals 128*a* and 128*b* are electrically connected to the adapter terminals 114*a* and 114*b*, respectively.

Heat-radiating member accommodation holes 120*e* are formed at regular intervals on the proximal surface of the objective holder 120. The number of holes 120*e* is predetermined. In the holes 120*e*, the bundle members 129, serving as heat-radiating members for radiating heat conducted through the objective holder 120, are arranged. Each bundle member 129 is formed in consideration of flexibility by making a plurality of wires 129*a*, such as copper wires, aluminum wires, or silver wires, into a bundle. Each wire 129*a* has a high thermal conductivity and a diameter of 0.1 mm or smaller. The number of wires 129*a* and the length of each wire 129*a* are properly set in consideration of heat capacity and workability depending on the type of endoscope.

Both ends of each bundle member 129, i.e., the distal and proximal ends of wires 129*a* included in each member 129 are united in consideration of the workability by, e.g., soldering or brazing, or using adhesive. According to the fourth embodiment, eight united portions are arranged in the holes 120*e*, respectively.

Each of the first to third connecting tubes 121 to 123 is made of a highly corrosion resistant metal having a low thermal conductivity, such as stainless steel. An external thread segment 121*a* is formed on the outer surface of the first connecting tube 121, the external thread segment 121*a* being screwed into the internal thread segments 117*a* in the ring member 117.

The second connecting tube 122 is tubular and includes a large-diameter portion 122*a* and a small-diameter portion 122*b* on which the first and third connecting tubes 121 and 123 are integrally arranged. Specifically, the inner surface of the proximal end portion of the first connecting tube 121 is integrally fitted on the outer surface of the distal end portion of the large-diameter portion 122*a* of the second connecting tube 122. The inner surface of the distal end portion of the third connecting tube 123 is integrally fitted on the outer surface of the small-diameter portion 122*b* thereof.

The third connecting tube 123 is substantially tubular. The second connecting tube 122 and the bending portion 107 are integrally arranged on the third connecting tube 123. Specifically, the outer surface of the small-diameter portion 122*b* of the second connecting tube 122 is integrally fitted on the inner surface of the distal end portion of the third connecting tube 123. In predetermined positions in the proximal end portion of the third connecting tube 123, distal-end bending pieces 105*a*, a bending rubber 105*b*, and an external blade 105*c* which constitute the bending portion 107 are arranged. The bending rubber 105*b* and the external blade 105*c* are integrally fixed to the third connecting tube 123 by winding fixing members 105*d*. Downward and upward bending wires 105*e* and 105*f* are arranged in the bending portion 107.

The observation optical unit 124 includes, e.g., optical lenses 124*a* to 124*c*. The optical lenses 124*a* to 124*c* are fixed to the lens frame 125. A cover glass 127*b* constituting the image pickup device 127, which includes the lens frame 125 and a CCD 127*a*, is fixed to the main frame 126. Terminals 127*c* extending from the proximal end of the CCD 127*a* are electrically connected to signal lines 131 in predetermined positions, the signal lines 131 passing through a signal cable 130.

The main frame 126 is integrally fixed to the objective holder 120 by a fastening screw 135. Each of the lens frame 125 and the main frame 126 is made of a highly corrosion resistant metal having a low thermal conductivity, such as stainless steel.

The insertion-unit terminals 128a and 128b are metallic components constituting a second electric connecting unit. The insertion-unit terminals 128a and 128b have distal recesses 128c, serving as contacts to be come into electrical contact with the elastic contacts 114c of the adapter terminals 114a and 114b, respectively. The proximal ends of the insertion-unit terminals 128a and 128b are electrically connected to power supply cables 132 and 133 for supplying power to the LED illumination lights 118, respectively. Insulating members 134a and 134b are arranged on the outer circumferences of the insertion-unit terminals 128a and 128b, respectively.

The eight bundle members 129 extending toward the proximal end of the endoscope are combined in the vicinity of the bending portion 107 such that two adjacent bundle members 129 are combined into one bundle (not shown). The combined bundle members 129, passing through the bending portion 107, are arranged in the flexible tube 108. The flexible tube 108 includes a spiral tube (not shown) arranged on the inner surface of the tube 108, a mesh tube (not shown) covering the spiral tube, and an external tube (not shown) covering the mesh tube. An O-ring 136 makes the connection between the direct-view type distal-end adapter 103 and the distal end portion 106 of the insertion unit 102 watertight.

Figure 37:
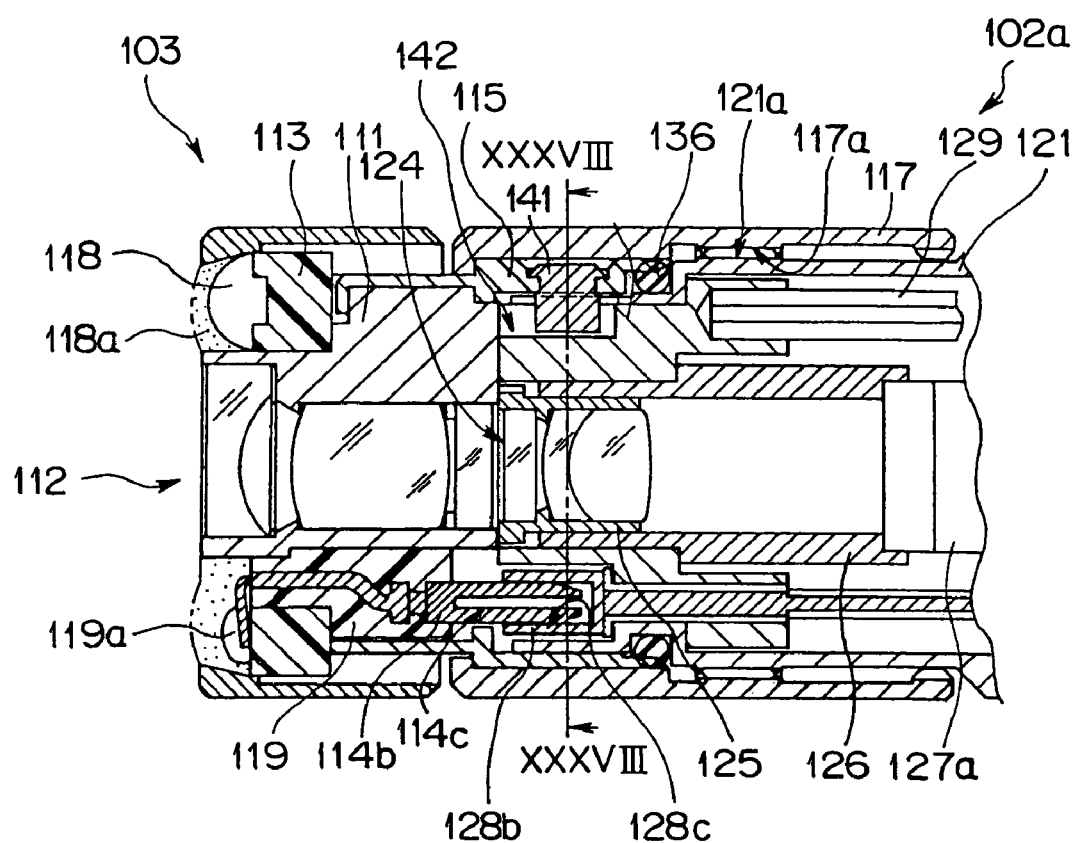
FIG. 37 is a diagram showing the direct-view type distal-end adapter attached to the distal end portion.
Figure 38:
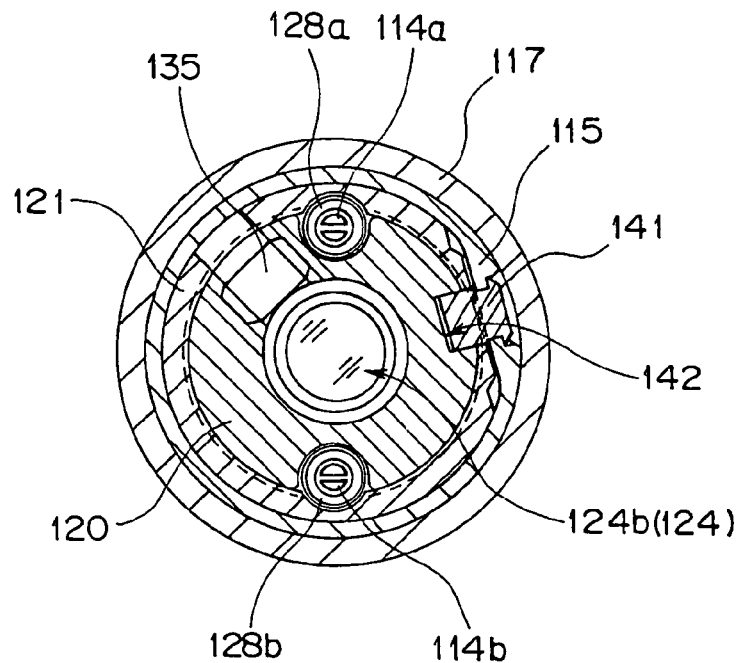
FIG. 38 is a sectional view at the line XXXVIII-XXXVIII of FIG. 37.

A process of connecting the direct-view type distal-end adapter 103 to the distal end portion 106 will now be described with reference to FIGS. 36 to 38.

Figure 36:
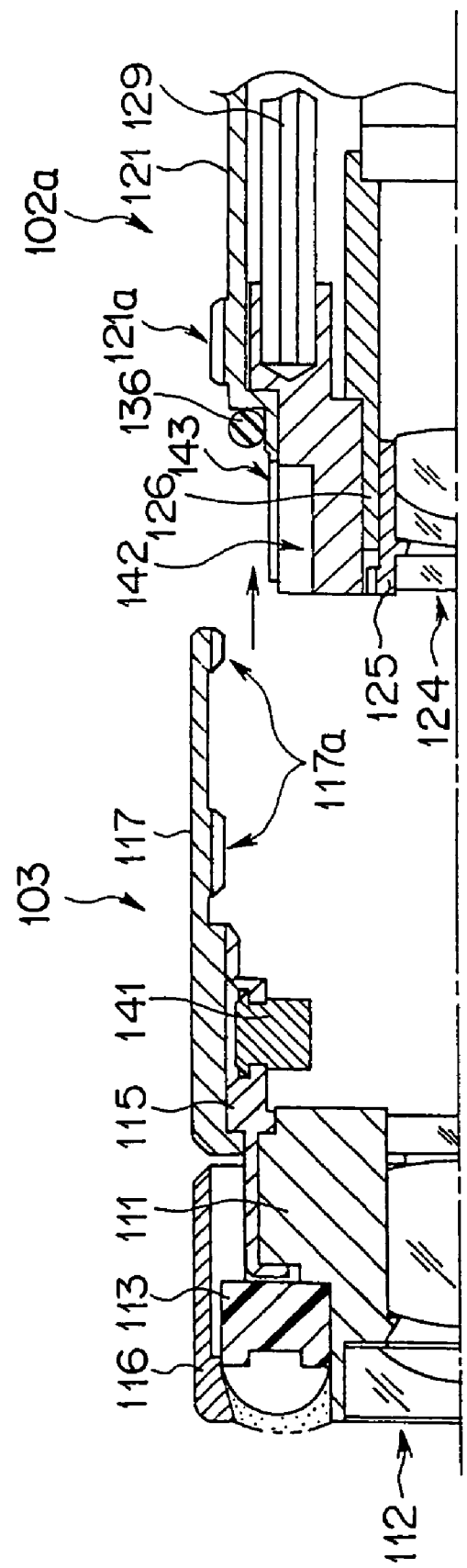
FIG. 36 is a diagram explaining the positional relationship between the direct-view type distal-end adapter shown in the sectional view at the line XXXVI-XXXVI of FIG. 27 and the distal end portion shown in the sectional view at the line XXXVI-XXXVI of FIG. 31.

Referring to FIG. 36, a positioning pin 141 is arranged in the adapter-body support member 115 constituting the direct-view type distal-end adapter 103. In addition, a positioning groove 142, which the positioning pin 141 is fitted into, is formed in the objective holder 120 constituting the distal end portion 106 of the insertion unit 102.

A notch 143 corresponding to the positioning groove 142 is formed in a predetermined position in the first connecting tube 121.

To attach the direct-view type distal-end adapter 103 to the distal end portion 106, the one internal thread segment 117a formed in the end portion of the ring member 117, constituting the direct-view type distal-end adapter 103, is made facing the external thread segment 121a formed at the first connecting tube 121, constituting the distal end portion 106. The external thread segment 121a is screwed into the internal thread segment 117a and, after that, the ring member 117 is rotated in a predetermined direction. Thus, the internal thread segment 117a crosses the external thread segment 121a, so that the direct-view type distal-end adapter 103 is loosely fitted to the distal end portion 106.

In this state, the positioning pin 141 on the direct-view type distal-end adapter 103 and the positioning groove 142 formed in the distal end portion 106 are made facing. Then, the positioning pin 141 is inserted into the positioning groove 142. In this state, the direct-view type distal-end adapter 103 is slid in the longitudinal direction.

Consequently, the elastic contacts 114c of the adapter terminals 114a and 114b are inserted into the distal recesses 128c of the insertion-unit terminals 128a and 128b, respectively. In this state, the direct-view type distal-end adapter 103 is further slid along the positioning groove 142 in the longitudinal direction. Thus, the elastic contacts 114c of the adapter terminals 114a and 114b are arranged deep in the distal recesses 128c in the distal end portions of the insertion-unit terminals 128a and 128b, so that the external thread segment 121a faces the internal thread segment 117a.

The ring member 117 is rotated in a predetermined direction. Thus, the external thread segment 121a is screwed into the other internal thread segment 117a, so that the direct-view type distal-end adapter 103 is moved in the longitudinal direction. Consequently, as shown in FIGS. 37 and 38, attaching of the direct-view type distal-end adapter 103 to the distal end portion 106 is complete.

In this instance, the elastic contacts 114c of the adapter terminals 114a and 114b are arranged in the distal recesses 128c of the insertion-unit terminals 128a and 128b, respectively, in a predetermined state. In addition, the objective optical unit 112 and the observation optical unit 124 are aligned such that the optical axis of the unit 112 substantially coincides with that of the unit 124. Further, the proximal surface of the adapter body 111 is in contact with the distal-end surface of the objective holder 120.

In this state, the LED illumination lights 118 are supplied with power through the power supply cables 132 and 133. The LED illumination lights 118 arranged in the LED substrate 113 are turned on, thus illuminating an observation area. Consequently, the optical image of the observation area illuminated by the illumination rays is formed on the surface of the CCD 127a through the optical lenses 112a to 112c of the objective optical unit 112 and those 124a to 124c of the observation optical unit 124, thus obtaining an endoscopic image.

The LED illumination lights 118 are continuously supplied with power, so that heat generated from the LED illumination lights 118 is gradually transferred to the LED substrate 113. Thus, the temperature of the LED illumination lights 118 gradually increases. The heat conducted through the LED substrate 113 is further transferred to the adapter body 111, the objective holder 120 in tight contact with the adapter body 111, and the bundle members 129 arranged on the proximal surface of the objective holder 120. The heat is transferred from the distal ends of the bundle members 129 in the direction toward the proximal ends and is then radiated.

As mentioned above, heat generated by the LED illumination lights in the direct-view type distal-end adapter is transmitted from the distal ends of the bundle members in the direction toward the proximal ends through the LED substrate, the adapter body, and the objective holder. Advantageously, the LED illumination lights can be prevented from being exposed to a high temperature.

Heat generated by the LED illumination lights is radiated. In addition, the lens frame and the image pickup frame (main frame) are made of a metal having a low thermal conductivity, such as stainless steel. Thus, the conduction of heat generated by the LED illumination lights to the CCD can be prevented with reliability.

Consequently, an observation area is illuminated by the desired amount of light for a long time using LED illumination lights to obtain good endoscopic images without noises, with which endoscopic observation can be performed.

According to the present embodiment, the direct-view type distal-end adapter has the positioning pin and the positioning groove is formed in the distal end portion of the insertion unit. Advantageously, the positional relationship between the direct-view type distal-end adapter and the distal end portion can be uniquely defined. Thus, the incorrect connection between the insertion-unit terminals and the adapter terminals can be surely prevented.

In addition, the position of the positioning pin is set such that the adapter terminals are electrically connected to the insertion-unit terminals by fitting the positioning pin into the positioning groove and then sliding the direct-view type distal-end adapter in the longitudinal direction. Advantageously, in attaching the direct-view type distal-end adapter to the distal end portion of the insertion unit, a trouble, e.g., the breakage of any adapter terminal or insertion-unit terminal can be reliably prevented.

According to the present embodiment, the electric connection between the adapter terminals 114 and the insertion-unit terminals 128 is achieved by inserting the elastic contacts 114c into the distal recesses 128c in the distal end portion 106 on condition that the direct-view type distal-end adapter 103 is attached to the distal end portion 106. The electric connection between the adapter terminals 114 and the insertion-unit terminals 128 is not limited to the insertion of the elastic contacts 114c into the distal recesses 128c. The following structures shown in FIGS. 39 to 43 may be used.

Figure 39:
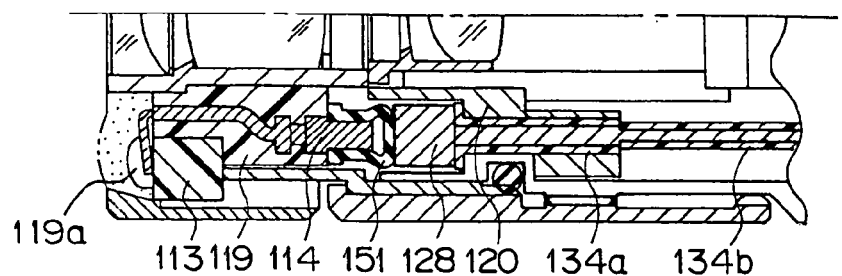
FIG. 39 is a diagram explaining the structure of another connection between each adapter terminal and the corresponding insertion-unit terminal.

In the structure of FIG. 39, an electric conductive rubber 151 is arranged at the proximal end of each adapter terminal 114. The electric conductive rubber 151 is come into tight contact with the flat surface of the corresponding insertion-unit terminal 128 to achieve the electric connection therebetween.

Figure 40:
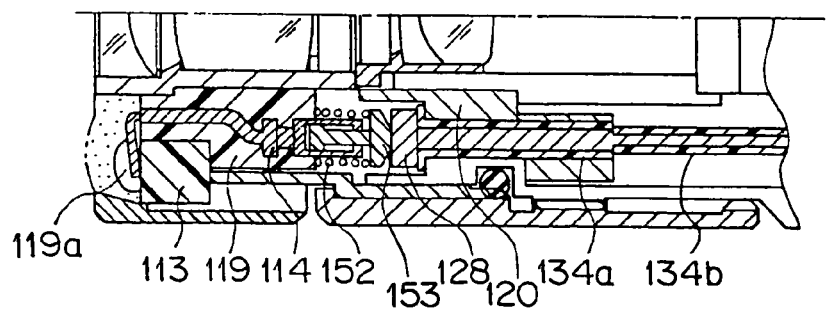
FIG. 40 is a diagram explaining the structure of another connection between each adapter terminal and the corresponding insertion-unit terminal.

In the structure of FIG. 40, a coil spring 152, functioning as biasing means, is arranged at the proximal end of each adapter terminal 114. A sliding terminal 153 having a convex surface is spring-biased to the flat surface of the corresponding insertion-unit terminal 128 by the coil spring 152, thus achieving the electric connection therebetween.

Figure 41:
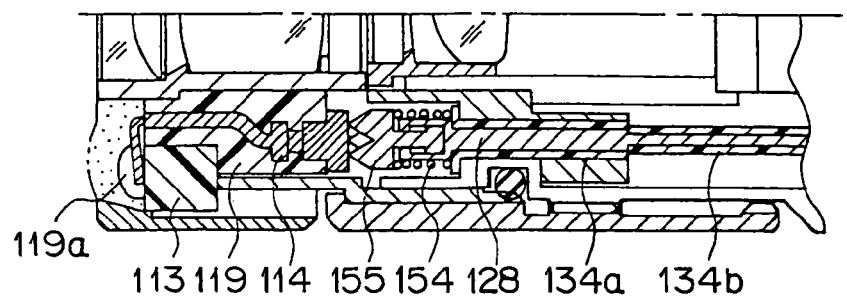
FIG. 41 is a diagram explaining the structure of another connection between each adapter terminal and the corresponding insertion-unit terminal.

In the structure of FIG. 41, a coil spring 154, functioning as biasing means, is arranged at the distal end of each insertion-unit terminal 128. A sliding terminal 155, of which end face has projections like contact pins, is spring-biased to the flat surface of the corresponding adapter terminal 114 by the coil spring 154, thus achieving the electric connection therebetween.

Figure 42:
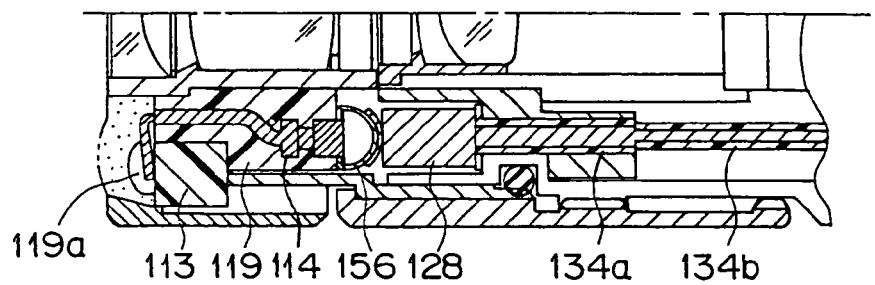
FIG. 42 is a diagram explaining the structure of another connection between each adapter terminal and the corresponding insertion-unit terminal.

In the structure of FIG. 42, a plate spring 156 having a semicircular cross section is arranged as an electrical contact having biasing means at the proximal end of each adapter terminal 114. The plate spring 156 is spring-biased to the flat surface of the corresponding insertion-unit terminal 128 to achieve the electric connection therebetween.

Figure 43:
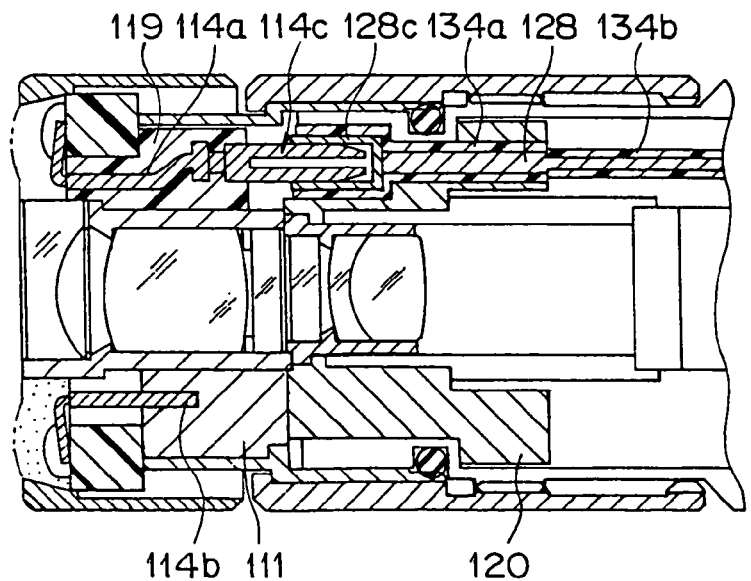
FIG. 43 is a diagram explaining the structure of another connection between each adapter terminal and the corresponding insertion-unit terminal.

In the structure of FIG. 43, the positive adapter terminal 114a is connected to the insertion-unit terminal 128 and the negative adapter terminal 114b is grounded to the adapter body 111, serving as a casing, thus achieving the electric connection between the adapter and the insertion unit.

Figure 44:
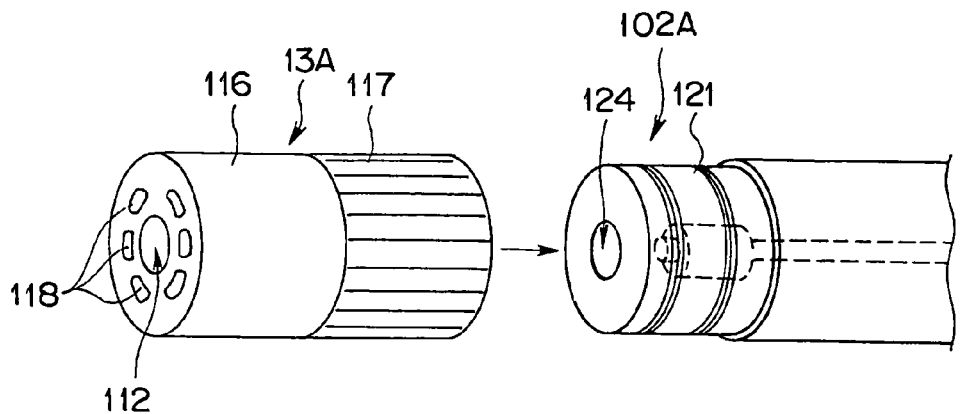
FIG. 44 is a diagram explaining an example of the arrangement of LED illumination lights in a direct-view type distal-end adapter.
Figure 45:
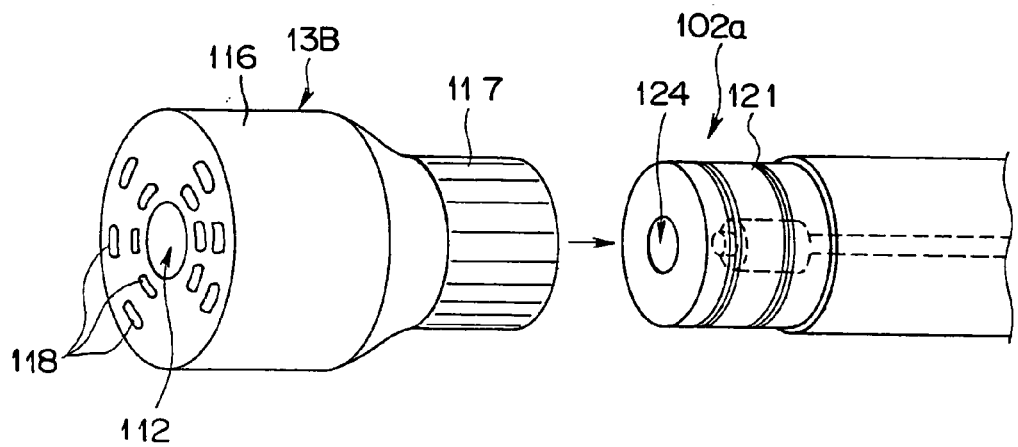
FIG. 45 is a diagram explaining an example of another arrangement of LED illumination lights in a direct-view type distal-end adapter.
Figure 46:
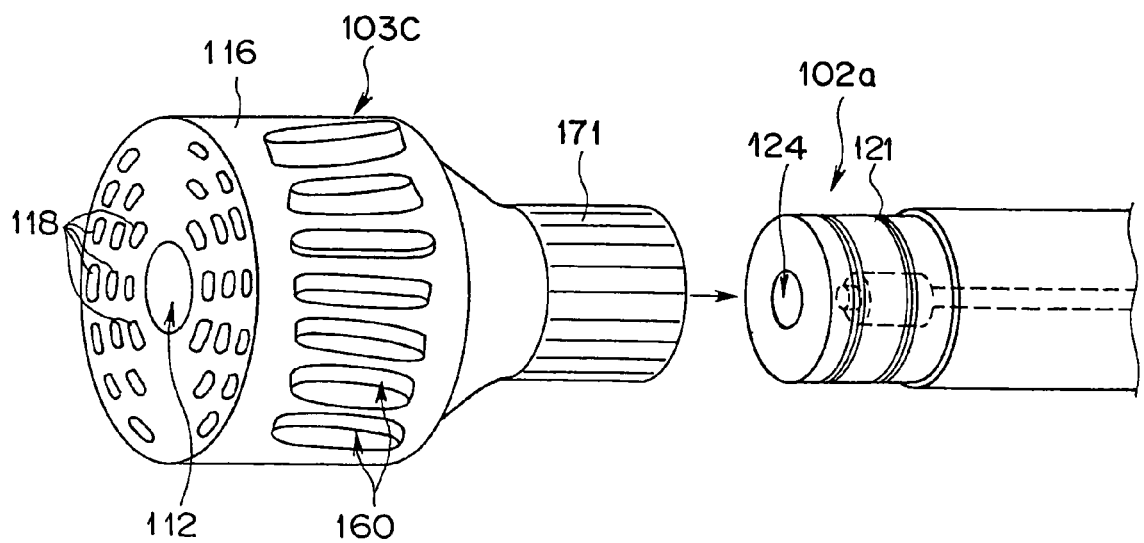
FIG. 46 is a diagram explaining an example of another arrangement of LED illumination lights in a direct-view type distal-end adapter.

According to the fourth embodiment, the eight LED illumination lights 118 are arranged at regular intervals on a circumference at a predetermined distance from the center of the distal-end surface of the direct-view type distal-end adapter 103. The arrangement of the LED illumination lights 118 is not limited to the above. However, as shown in FIGS. 44 to 46, various arrangement patterns are available. Referring to FIG. 44, a direct-view type distal-end adapter 103A has, e.g., six LED illumination lights 118 arranged at regular intervals on a circumference at a predetermined distance from the center of the end face of the adapter. Referring to FIG. 45, a direct-view type distal-end adapter 103B has LED illumination lights 118 arranged at regular intervals on two circumferences at predetermined distances from the center of the end face of the adapter. In each circle, six LED illumination lights 118 are arranged. Referring to FIG. 46, a direct-view type distal-end adapter 103C has LED illumination lights 118 arranged at regular intervals on three circumferences at predetermined distances from the center of the end face of the adapter. In the innermost circle, six LED illumination lights 118 are arranged. In the intermediate circle, ten LED illumination lights 118 are arranged. In the outermost circle, fourteen LED illumination lights 118 are arranged.

In the direct-view type distal-end adapter 103C of FIG. 46, a cooling fin 160 is arranged on the outer surface of the cover member 116 to dissipate heat generated by the LED illumination lights 118. Thus, the LED illumination lights 118 can be prevented from being exposed to a high temperature.

Figure 47:
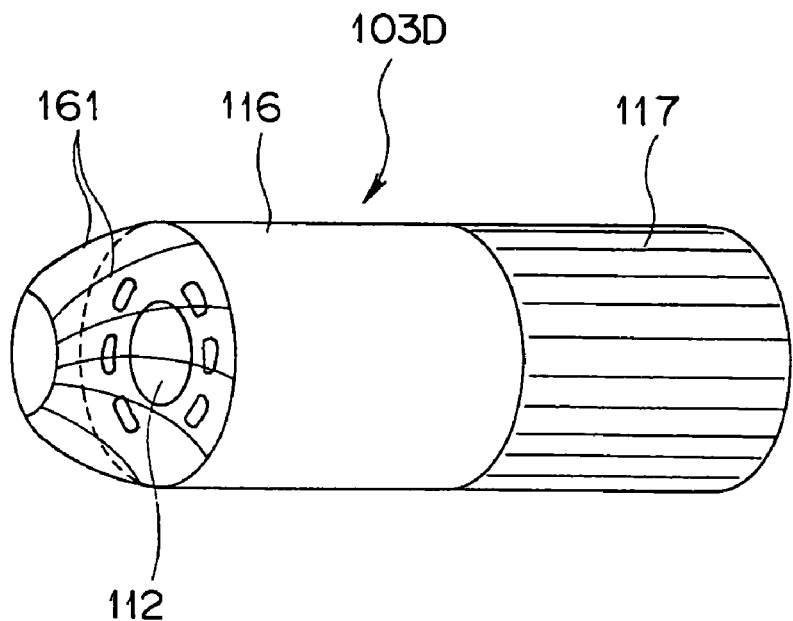
FIG. 47 is a diagram explaining a direct-view type distal-end adapter having a radial plate member in which a plurality of LED illumination lights are arranged.
Figure 48:
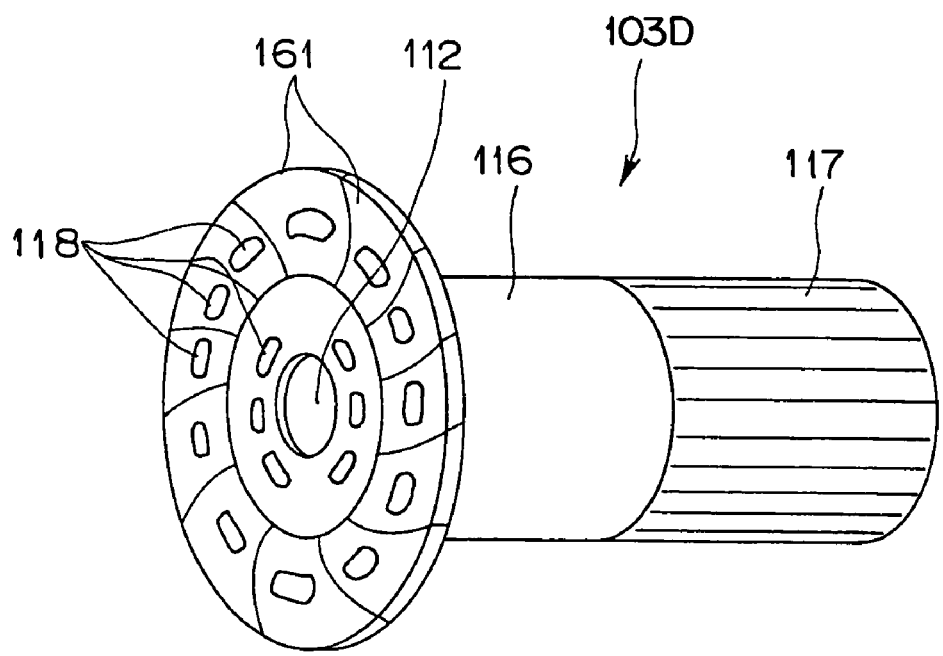
FIG. 48 is a diagram explaining the direct-view type distal-end adapter with the opened radial plate member having the LED illumination lights.
Figure 49:
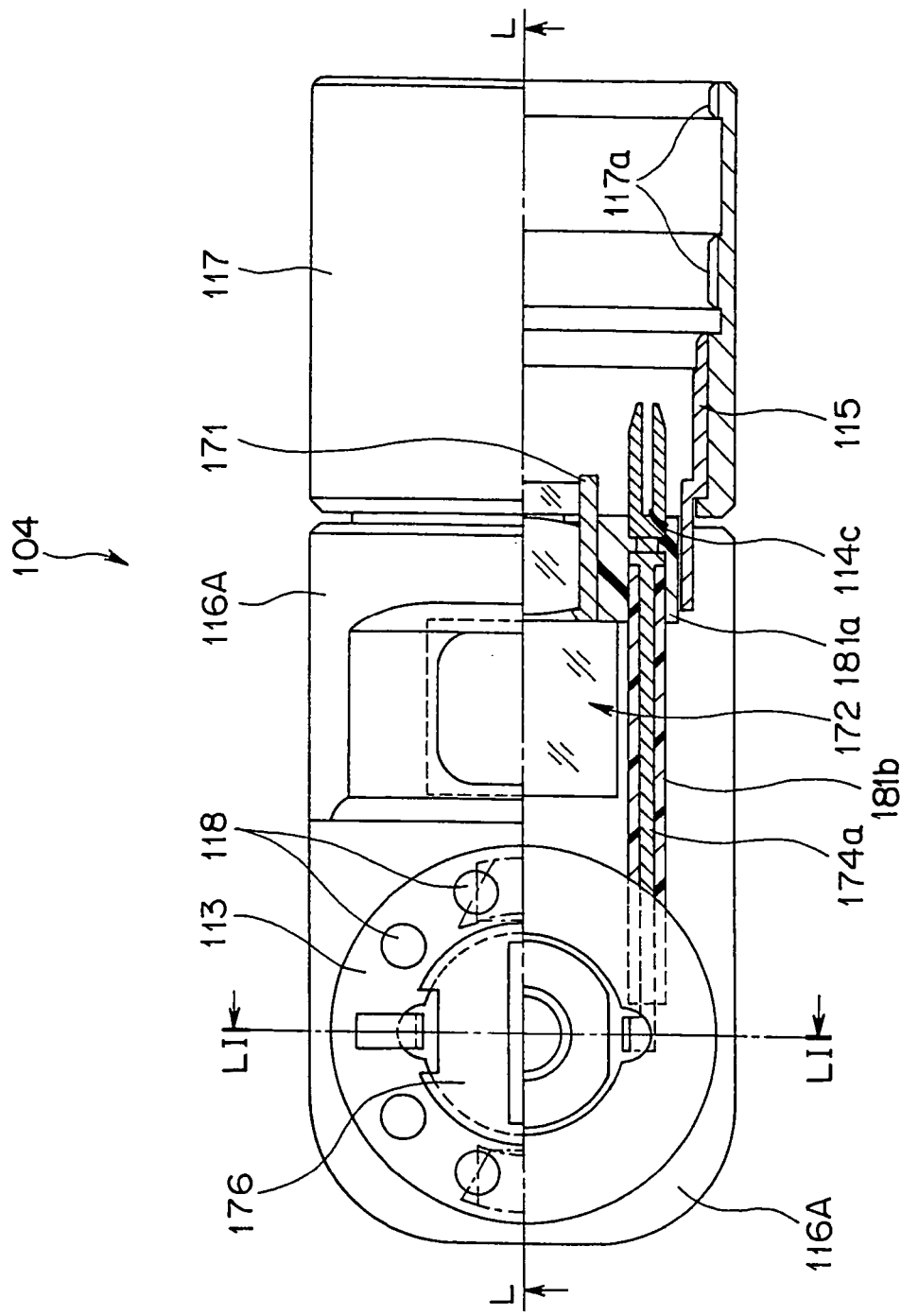
FIG. 49 is a diagram explaining a side-view type distal-end adapter.
Figure 50:
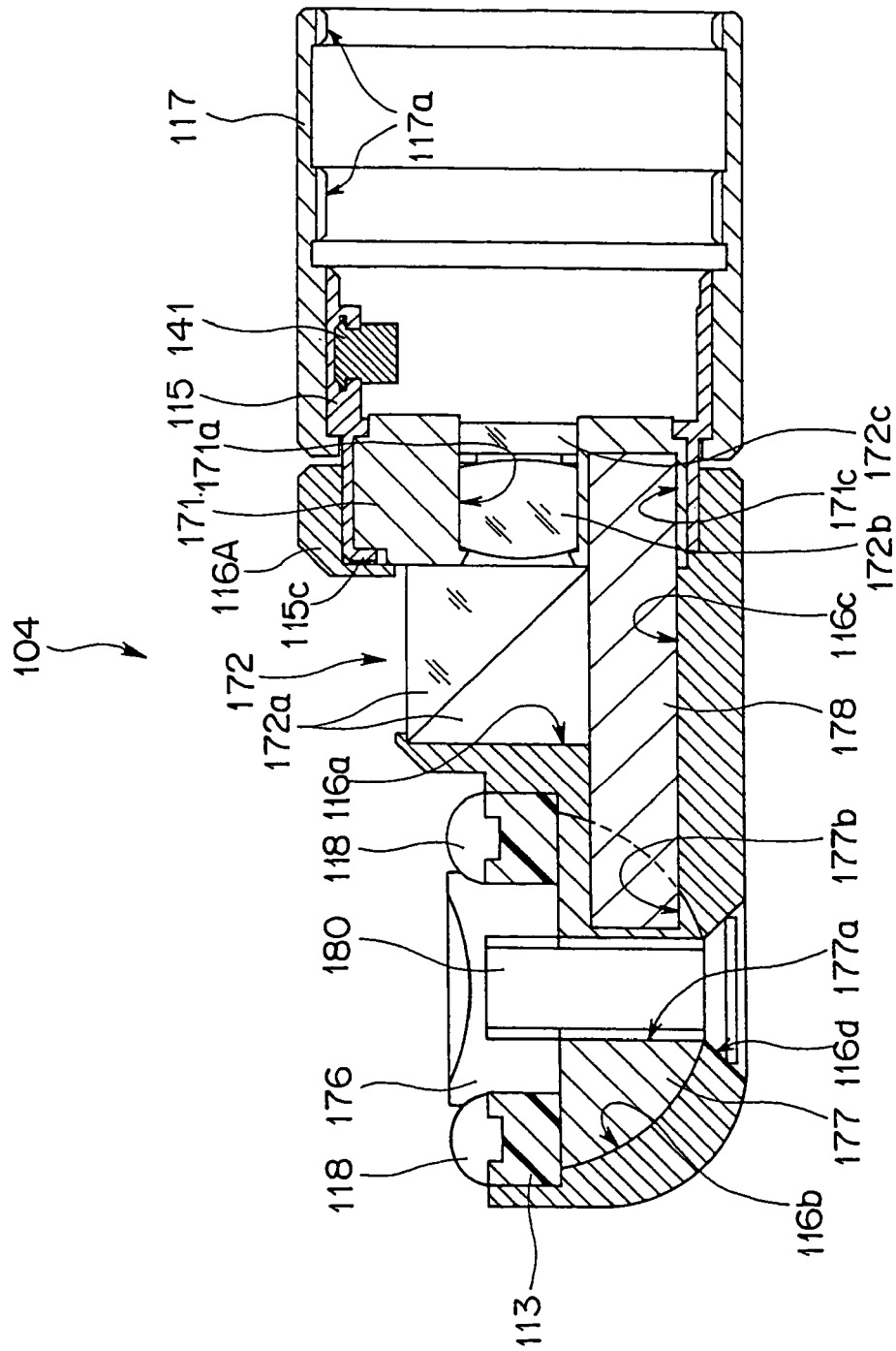
FIG. 50 is a sectional view at the line L-L of FIG. 49.
Figure 51:
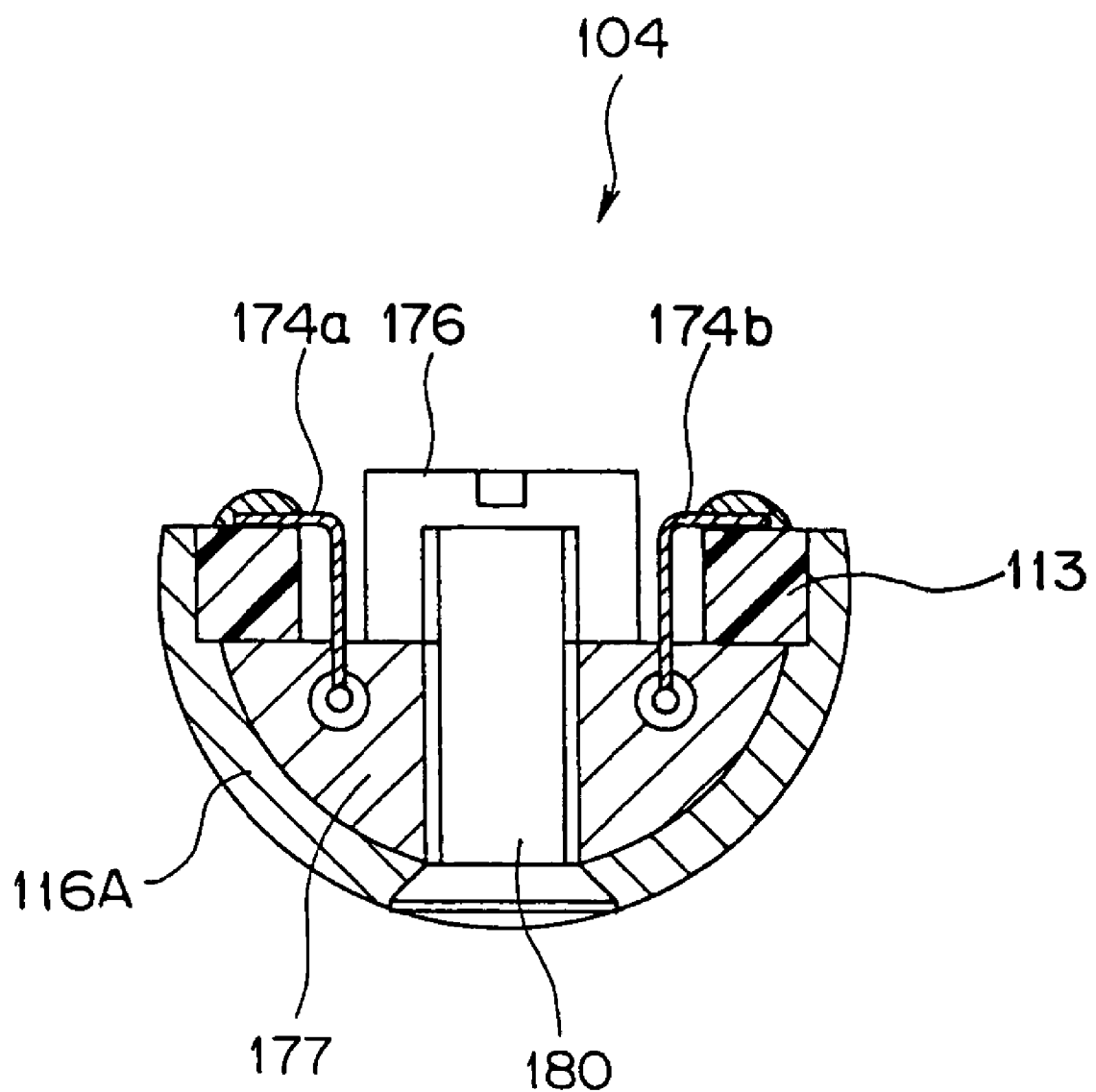
FIG. 51 is a sectional view at the line LI-LI of FIG. 49.

In addition, a radial plate member 161 having the LED illumination lights 118 on the inner surface may be arranged at the distal end of the cover member 116 as shown in FIG. 47. The radial plate member 161 is made of a shape memory alloy. The LED illumination lights 118 are supplied with power, so that the radial plate member 161 is deformed into a flaring shape, i.e., opened as shown in FIG. 48. Thus, the radial plate member 161 applies a large amount of illumination rays to an observation area.

The structure of the side-view type distal-end adapter 104 will now be described with reference to FIGS. 49 to 55.

The side-view type distal-end adapter 104 includes an adapter body 171, an objective optical unit 172, an LED substrate 113, a pair of adapter terminals 174a and 174b, an adapter-body support member 115, a cover member 116A, a retaining member 176, a ring member 117, a semispherical heat-conducting member 177, and a columnar heat-conducting member 178.

The adapter body 171 serves as a part of a first heat-conducting member and is made of a metal having a high thermal conductivity, such as copper or aluminum. The adapter body 171 is substantially tubular. In other words, a central through-hole 171a is formed in substantially the center of the adapter body 171. In addition, a pair of holes 171b for accommodating adapter terminals 174a and 174b and a hole 171c for accommodating the columnar heat-conducting member 178 are formed in the adapter body 171.

The objective optical unit 172 includes a mirror 172a that bends the optical axis at, e.g., a right angle and a plurality of optical lenses 172b and 172c, which are arranged in the central through-hole 171a.

The LED substrate 113 is, e.g., an aluminum circular plate having a central through-hole. The LED substrate 113 has a conductive pattern on one surface. In the conductive pattern, a plurality of LED illumination lights 118, serving as light emitting devices, and the one ends of the adapter terminals 174a and 174b are arranged. The LED substrate 113 is in tight contact with the flat surface of the semispherical heat-conducting member 177.

The adapter terminals 174a and 174b are a pair of metallic components constituting a first electric connecting unit. The other end of each of the adapter terminals 174a and 174b includes an elastic contact 114c having a notch.

The cover member 116A functions as a support made of a metal having a low thermal conductivity. The cover member 116A includes a recess 116a, a spherical recess 116b, and a hole 116c. In the recess 116a, the mirror 172a is arranged. In the spherical recess 116b, the semispherical heat-conducting member 177 is arranged. In the hole 116c, the columnar heat-conducting member 178 is arranged. In addition, the cover member 116A includes a countersink 116d which communicates with the spherical recess 116b.

Specifically, the retaining member 176 is fixed to the cover member 116A by a screw 180 passing through a through-hole 177a in the semispherical heat-conducting member 177 arranged in the spherical recess 116b, so that the semispherical heat-conducting member 177, the LED substrate 113, and the retaining member 176 are fixed to the cover member 116A.

The semispherical heat-conducting member 177 serves as a part of the first heat-conducting member and is made of a metal having a high thermal conductivity, such as copper or aluminum. The semispherical heat-conducting member 177 has the through-hole 177a, to which the screw 180 is inserted.

The columnar heat-conducting member 178 constitutes a part of the first heat-conducting member. The columnar heat-conducting member 178 is a rectangular or cylindrical column made of a metal having a high thermal conductivity, such as copper or aluminum. The columnar heat-conducting member 178 is arranged in the hole 116c of the cover member 116A.

The semispherical heat-conducting member 177 has a hole 177b which the end of the columnar heat-conducting member 178 is fitted into.

The other structure is the same as that of the direct-view type distal-end adapter 103. The same components as those of the adapter 103 are designated by the same reference numerals and a description thereof is omitted.

The side-view type distal-end adapter is constructed as mentioned above. When the external thread segment formed in the distal end portion of the first connecting tube is screwed into an internal thread segment formed on the ring member of the side-view type distal-end adapter, the adapter can be attached to the distal end portion of the endoscope. In this instance, the elastic contacts of the adapter terminals are fitted into the recesses of the insertion-unit terminals arranged in the distal end portion in a predetermined state.

Heat generated by the LED illumination lights is actively transferred to the LED substrate, the semispherical heat-conducting member, the columnar heat-conducting member, and the adapter body. After that, the heat is further transferred to the objective holder 120 and the bundle members 129 arranged in the distal end portion, so that the heat is radiated.

Consequently, the side-view type distal-end adapter 104 or the direct-view type distal-end adapter 103 can be selectively attached to the distal end portion 106.

When the side-view type distal-end adapter 104 is attached to the distal end portion 106, the optical characteristics of the endoscope with the side-view type distal-end adapter 104 are different from those of the endoscope with the direct-view type distal-end adapter 103 under observation. However, the same operation and advantages as those of the endoscope with the direct-view type distal-end adapter 103 can be obtained.

Figure 52:
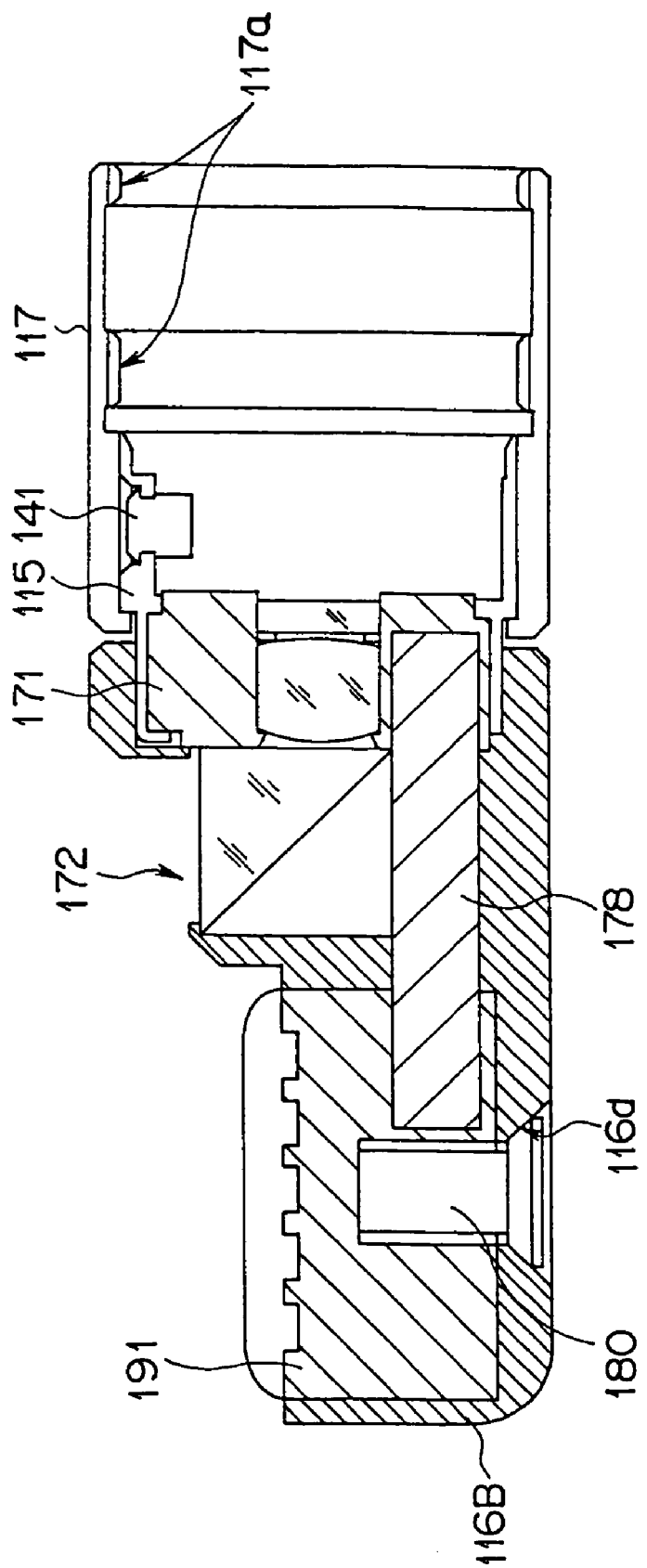
FIG. 52 is a longitudinal sectional view of another side-view type distal-end adapter.
Figure 53:
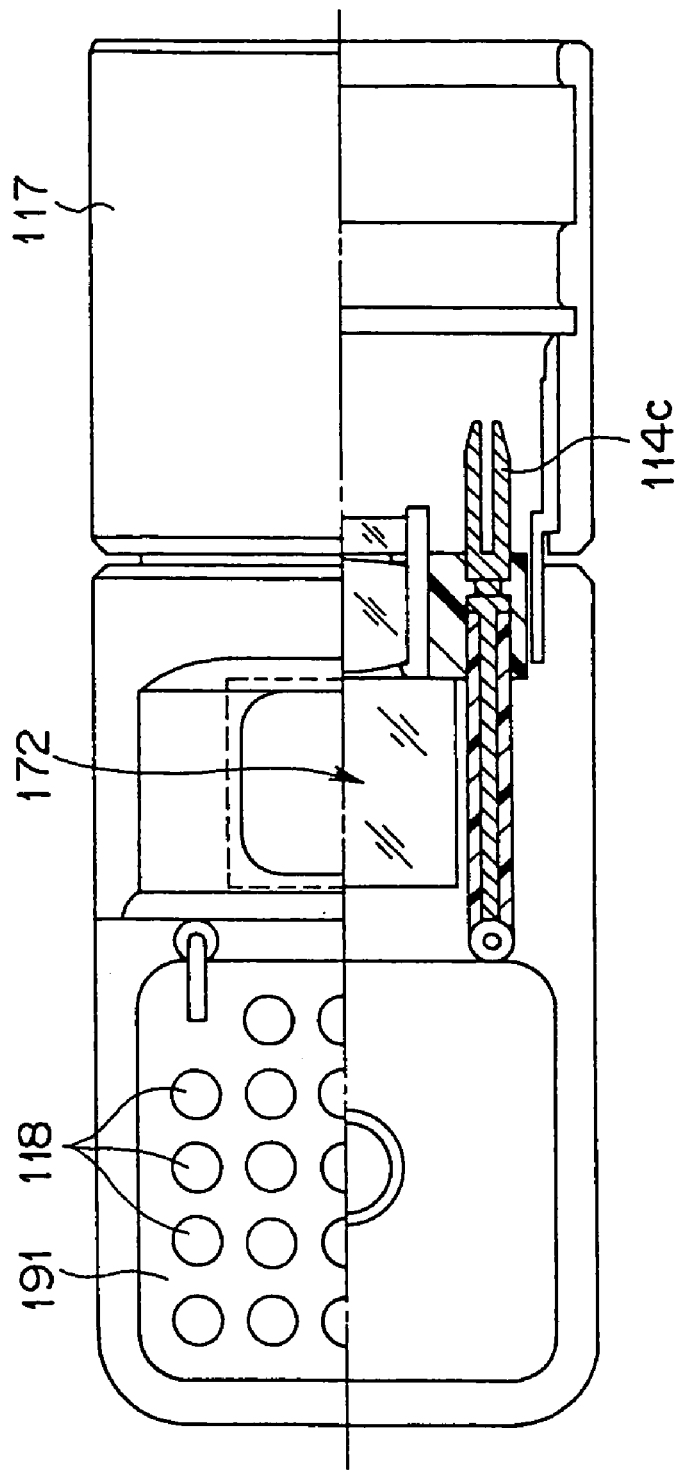
FIG. 53 is a front view of the side-view type distal-end adapter of FIG. 52.

As shown in FIGS. 52 and 53, an LED substrate 191 may be directly arranged in a cover member 116B so that heat generated by the LED illumination lights 118 is transferred through the LED substrate 191, the columnar heat-conducting member 178, and the adapter body 171 to the objective holder 120 and the bundle members 129 arranged in the distal end portion 106 to radiate the heat. In this case, the LED substrate 191 is rectangular and the LED illumination lights 118 are arranged in a matrix on one surface of the LED substrate 191. Thus, the same heat radiation effect as that in the foregoing structure can be obtained. In addition, the number of components can be reduced and the amount of illumination rays can be increased.

Figure 54:
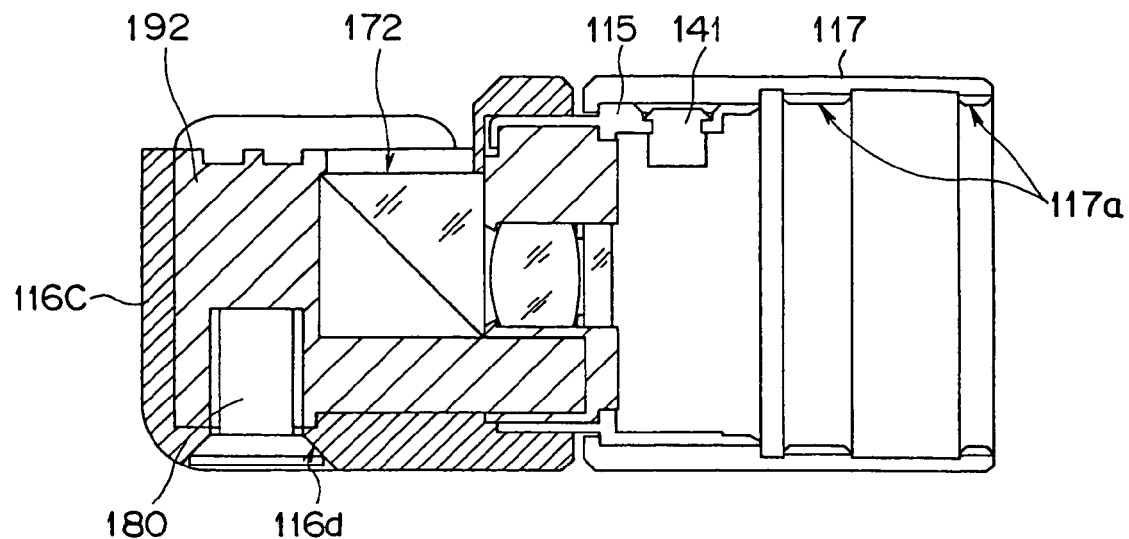
FIG. 54 is a longitudinal sectional view of another side-view type distal-end adapter.
Figure 55:
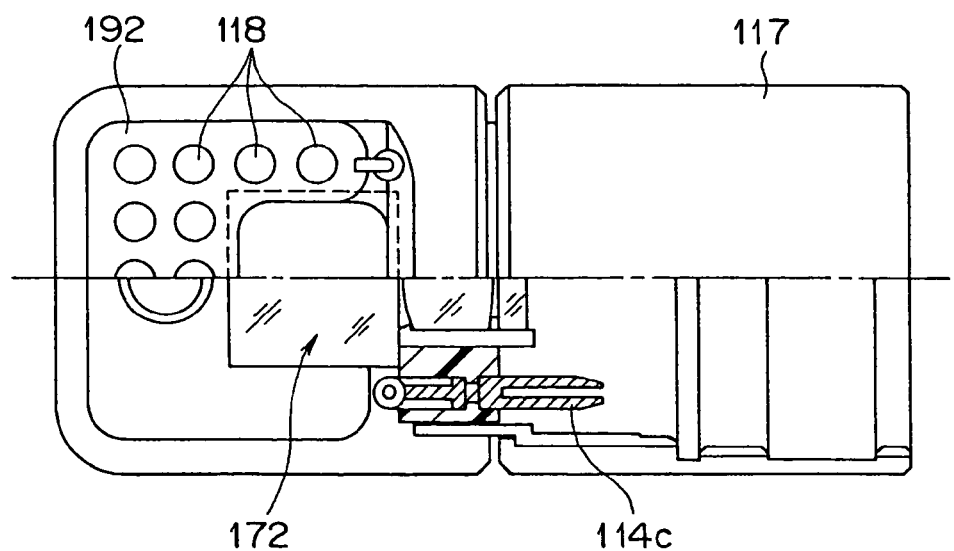
FIG. 55 is a front view of the side-view type distal-end adapter of FIG. 54.

As shown in FIGS. 54 and 55, an LED substrate 192 can be directly arranged in a cover member 116C. The LED substrate 192 may have a space in which the mirror 172a is arranged and the LED illumination lights 118 may be arranged in the vicinity of the mirror 172a. Thus, the same heat radiation effect as those of the foregoing structures can be obtained. In addition, the number of components can be reduced and the length of the side-view type distal-end adapter can be reduced.

According to the present embodiment, the direct-view type and side-view type distal-end adapters have been described. The distal-end adapter is not limited to the above types. A distal-end adapter of which field of view is set in another direction, e.g., an oblique forward view distal-end adapter may be used.

In the above-described embodiments, LEDs are used as light emitting devices. A light emitting device is not limited to an LED. A laser diode may be used.

The present invention is not limited to the above-described embodiments and various changes and modifications thereof may be made without departing from the spirit and scope of the invention.

What is claimed is:

1. An endoscope specifically comprising:
   a distal-end adapter including light emitting devices constituting an illumination optical system, a substrate for the light emitting devices, a support member for supporting the substrate, a first heat-conducting member through which heat generated by the light emitting devices is conducted, and an objective optical system constituting an observation optical system, the light emitting devices being arranged in one surface of the distal-end adapter, the substrate having a first electric connecting unit for the light emitting devices which is arranged in the other surface of the distal-end adapter; and
   an insertion unit having a distal end portion from which the distal-end adapter is detachable, the distal end portion including an image pickup device constituting the observation optical system, a second electric connecting unit which is electrically connected to the first electric connecting unit in the substrate, a second heat-conducting member through which the heat transferred through the first heat-conducting member is further conducted, and a heat-radiating member for radiating the heat conducted through the second heat-conducting member from the distal end portion in the direction toward the proximal end of the endoscope.

2. The endoscope according to claim 1, wherein the heat-radiating member has a uniform cross section.

3. The endoscope according to claim 1, wherein the length of the heat-radiating member is set in consideration of the material and cross section thereof.

4. The endoscope according to claim 1, wherein
   the insertion unit is flexible and includes a bending portion, and
   the heat-radiating member includes a bundle member formed by tying wires in a bundle, each wire having a diameter of 0.1 mm or smaller.

5. The endoscope according to claim 4, wherein
   the bundle member extends from the vicinity of the light emitting devices in the direction toward the proximal end of the endoscope, and
   the bundle member is divided into segments in at least the bending portion.

6. The endoscope according to claim 4, wherein each wire is made of a material having a high thermal conductivity.

7. The endoscope according to claim 1, wherein
   the insertion unit is rigid, and
   the heat-radiating member is a rod member.

8. The endoscope according to claim 7, wherein the rod member is made of a material having a high thermal conductivity.

9. The endoscope according to claim 1, wherein the objective optical system of the distal-end adapter is a direct view type.

10. The endoscope according to claim 1, wherein the objective optical system of the distal-end adapter is a side view type.

11. The endoscope according to claim 1, further comprising:
electric-connection guiding means, arranged at the distal-end adapter and the distal end portion of the insertion unit, for electrically connecting the first and second electric connecting units in a predetermined relation.

12. The endoscope according to claim 1, wherein the substrate is in tight contact with the first heat-conducting member.

13. The endoscope according to claim 1, wherein one surface of the substrate includes a conductive pattern, and the light-emitting devices and one end of the first electric connecting unit are arranged in the conductive pattern.

* * * * *